United States Patent [19]
Crandall

[11] Patent Number: 5,830,909
[45] Date of Patent: Nov. 3, 1998

[54] ANGIOTENSIN (AII) ANTAGONISTS AS INHIBITORS OF THE GROWTH OF ADIPOSE TISSUE

[75] Inventor: David LeRoy Crandall, Cornwall, N.Y.

[73] Assignee: American Cyanamid Company, Madison, N.J.

[21] Appl. No.: 684,609

[22] Filed: Jul. 19, 1996

Related U.S. Application Data

[63] Continuation of Ser. No. 82,562, Jun. 28, 1993, abandoned.

[51] Int. Cl.$^6$ .................................................. A61K 31/41
[52] U.S. Cl. .................. 514/381; 514/382; 514/224.2; 514/253; 514/252; 514/404; 514/405; 514/212; 514/909
[58] Field of Search ........................ 514/381, 382, 514/222.4, 253, 252, 404, 405, 212, 909

[56] References Cited

U.S. PATENT DOCUMENTS

| | | | |
|---|---|---|---|
| 5,175,164 | 12/1992 | Bagley et al. | 514/381 |
| 5,260,325 | 11/1993 | Markwalder et al. | 514/381 |
| 5,266,583 | 11/1993 | Ohtawa | 514/381 |
| 5,274,104 | 12/1993 | Arnaud et al. | 514/381 |
| 5,376,666 | 12/1994 | Duncia | 514/381 |
| 5,380,739 | 1/1995 | Clark et al. | 514/381 |

OTHER PUBLICATIONS

D. G. Beevers et al., Br. J. Clin. Pharmac. 18:51–56 (1984).
C. Richer et al., Eur. J. Pharmac. 79:23–29 (1982).
Crandall et al., Metabolism 42:511–515 (1993).

*Primary Examiner*—James H. Reamer
*Attorney, Agent, or Firm*—Arthur G. Seifert

[57] ABSTRACT

The invention is a method of using Angiotensin (AII) Antagonists as inhibitors of the growth of adipose tissue, reducing adipocyte growth and body weight gain.

37 Claims, 3 Drawing Sheets

EQUILIBRIUM BINDING OF $^{125}$I-AII TO ADIPOCYTE MEMBRANES

REVERSIBLE BINDING OF $^{125}$I-AII TO ADIPOCYTE MEMBRANES

ANGIOTENSIN (AII) ANTAGONISTS AS INHIBITORS OF THE GROWTH OF ADIPOSE TISSUE

This is a continuation of application Ser. No. 08/082,562 filed Jun. 28, 1993, abandoned.

FIELD OF THE INVENTION

The invention relates to the use of Angiotensin (AII) Antagonists as inhibitors of the growth of adipose tissue, reducing adipocyte growth and body weight gain.

BACKGROUND OF THE INVENTION

Angiotensin is a well characterized peptide involved in cardiovascular homeostasis. For decades, angiotensin has been known to be a potent vaso-constrictor with profound effects on blood pressure and electrolyte balance. The classic concept of control of angiotensin metabolism via renin release from the kidney has more recently been revised to include peripheral tissue sites. The observation of significant quantities of locally generated angiotensin II (AII) from peripheral tissues has also coincided with data indicating that AII can act as a growth factor in cell culture systems and stimulate angiogenesis in vivo.

Membrane receptors for angiotensin II have been identified in many tissues from diverse species and the gene encoding the receptor protein has recently been cloned. Two subtypes of receptor have been observed, the high affinity $AT_1$ subtype typically found in vascular cells, and the low affinity $AT_2$ subtype found in nervous tissue. The angiotensinogen gene has been identified by in situ hybridization in brown adipose tissue and whole body autoradiographic techniques have indicated that AII receptors decrease in specific tissues during fetal development. Presently, AII has been characterized as both a potent vasoconstrictor, and an effector of growth and differentiation. To date, however, the functions of AII in addition to those producing cardiovascular effects have been proposed, but remain largely unresolved.

Adipose tissue is highly vascularized, and is one of the few tissues that can continue to expand through most of adult life. Angiotensinogen mRNA has been observed in whole adipose tissue preparations containing vascular, connective and fat cells, and isolated adipocytes incubated in the presence of exogenous angiotensin II release prostacyclin in a dose-dependent manner. In addition, for the first time, the receptor for AII in the rat fat cells has recently been identified, characterized in isolated adipocyte membranes and reported (D. L. Crandall et al., Metabolism, 42, 511–515 (1993).

SUMMARY OF THE INVENTION

The present invention relates to the identification of the AII receptor in adipocyte membranes and the use of angiotensin II receptor blocking agents to inhibit adipocyte AII receptors thereby reducing adipocyte growth and body weight gain. Accordingly, the invention also relates to the use of angiotensin II receptor blocking agents in treating diseases associated with adipocyte growth including obesity and non-insulin dependent diabetes mellitus.

Suitable therapeutic agents for the practice of this invention are those compounds which are known to have activity as angiotensin II receptor blocking agents and include various compounds of Formula I:

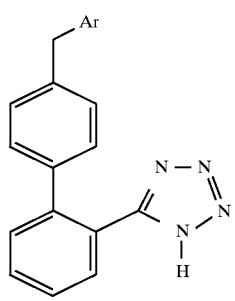

Formula I wherein:

Ar is selected from the group consisting of

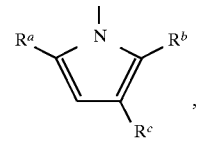

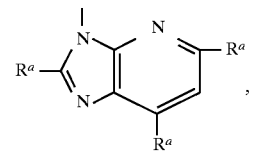

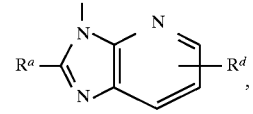

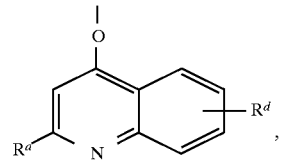

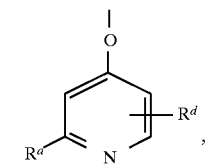

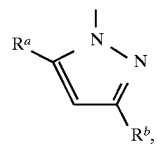

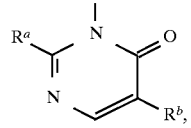

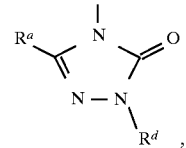

-continued

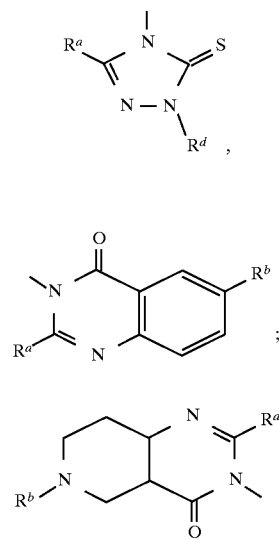

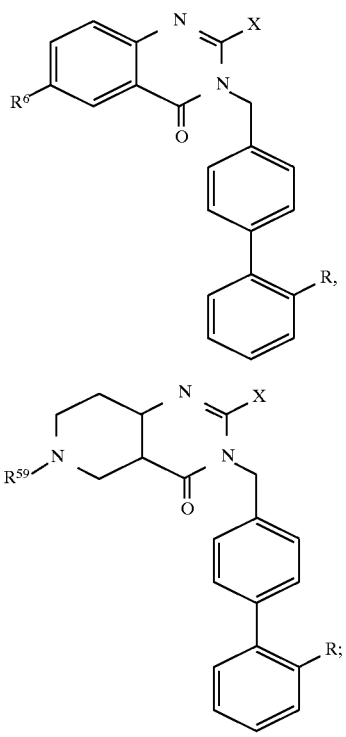

Formula II

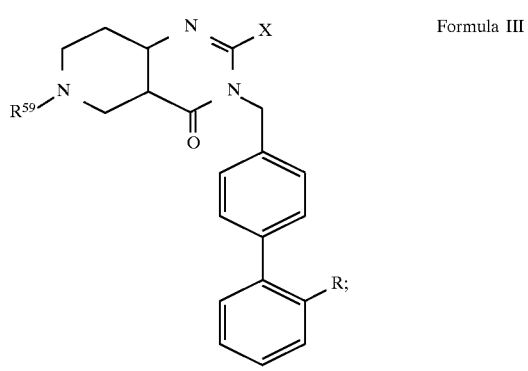

Formula III $R^a$ and $R^e$ are each independently lower alkyl of 1 to 5 carbon atoms;

$R^b$ is selected from:
(a) (C1–C6)alkyl optionally substituted with a substituent selected from the group consisting of hydroxy, (C1–C4)alkoxy, (C1–C4)alkyl, phenyl, substituted phenyl(substituent selected from (C1–C4)alkyl, CF$_3$, nitro, —NH$_2$, (C1–C4)alkoxy and halo), pyridine, thiophene, furan, —CHO, —COORf, —O—CORf, —CORf, —CON(Rf)2, and carboxymethylphenyl;
(b) a 5–15 membered monocyclic, bicyclic or tricyclic heterocyclic group wherein the heteroatom(s) are selected from 1–4 oxygen, sulfur or nitrogen atoms optionally substituted by (C1–C4)alkyl, (optionally substituted with —ORf, —CO$_2$Rf, —CN, —NH$_2$, —NHRf, —N(Rf)$_2$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —ORf, —CO$_2$Rf, —CN, —CF$_3$, —CON(Rf)$_2$, —SPh, —N(Rf) —

$R^c$ is hydrogen, halo or a pyrrole group attached at the nitrogen atom and unsubstituted or substituted by lower alkyl of 1 to 4 carbon atoms, Rd and Rf are independently selected from hydrogen and lower alkyl of 1 to 4 carbon atoms, a tautomer thereof and the pharmaceutically acceptable salts thereof.

Particularly preferred are various compounds of the Formulae II and III:

wherein:
R is —CO$_2$H, —NHSO$_2$CF$_3$ or

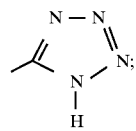

X is straight or branched alkyl of 3 to 5 carbon atoms;
$R^6$ is selected from the following moieties:

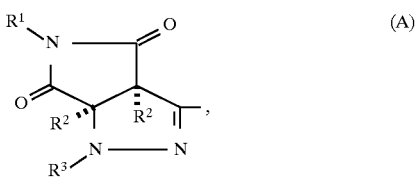
(A)

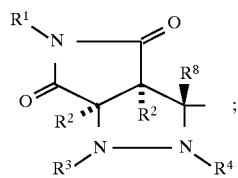

(B)

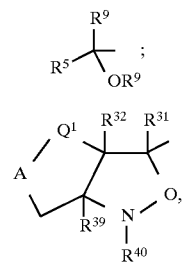

-continued
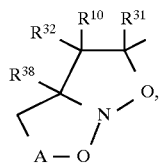
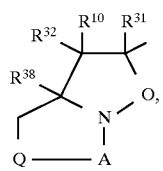
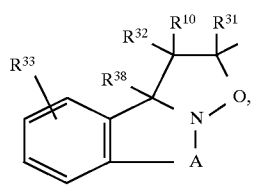
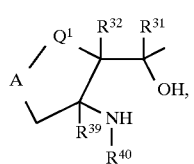 (C)
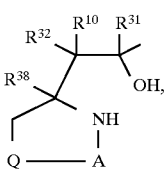
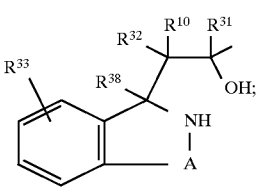
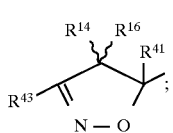 (D)
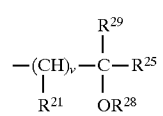 (E)
or
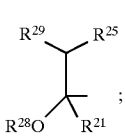
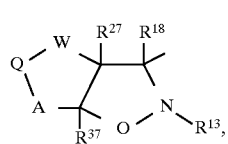
-continued
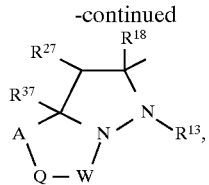
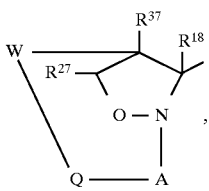 (F)
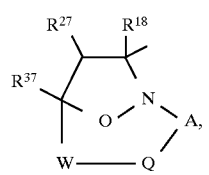
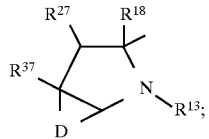
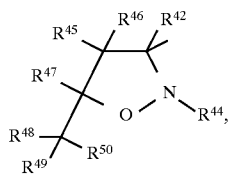 (G)
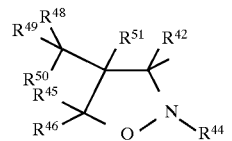
or
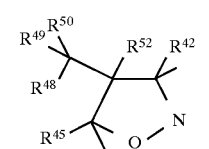
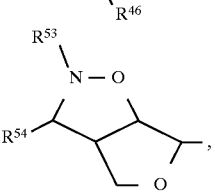
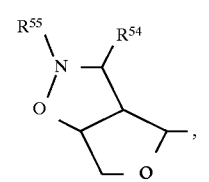

7
-continued
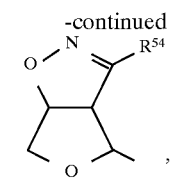
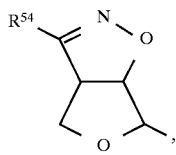
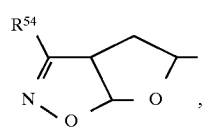 (H)
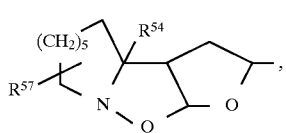
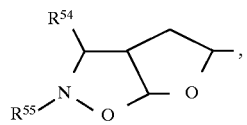
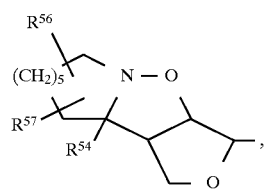
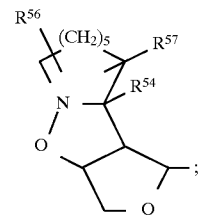
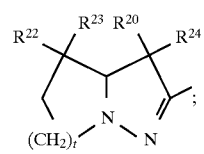 (I)
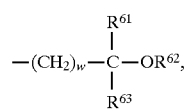
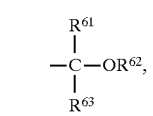
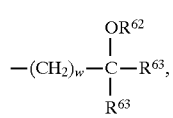
8
-continued
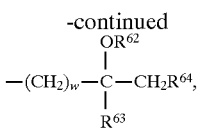
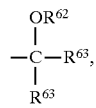 (J)
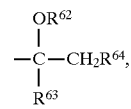
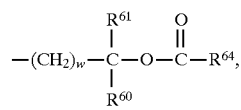
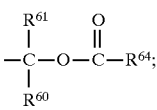
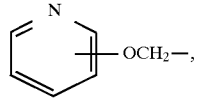 (K)
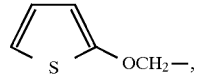
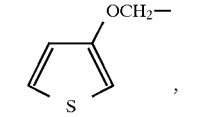
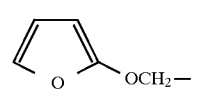
and
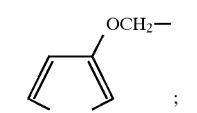
$R^{59}$ is selected from the following moieties:
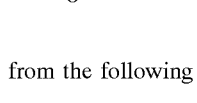 (L)
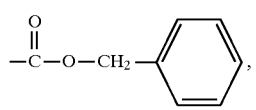
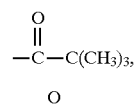
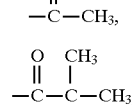

-continued

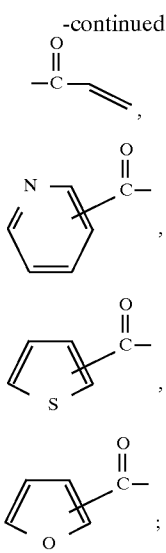

wherein:

(A) with reference to the moieties designated group (A) above:

$R^1$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), 2-pyridinyl, 4-pyridinyl, benzyl, substituted benzyl (substitution selected from mono-lower alkyl of 1 to 3 carbon atoms, trifluoromethyl, nitro, O-alkyl of 1 to 3 carbon atoms);

$R^2$ is H, and straight chain lower alkyl of 1 to 4 carbon atoms;

$R^3$ is H, triphenylmethyl, benzyl, substituted benzyl (substitution selected from mono-lower alkyl of 1 to 3 carbon atoms, trifluoromethyl, nitro, O-alkyl of 1 to 3 carbon atoms), straight chain lower alkyl of 1 to 4 carbon atoms;

$R^4$ is H, straight chain lower alkyl of 1 to 4 carbon atoms,

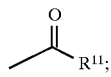

$R^{11}$ is lower alkyl of 1 to 3 carbon atoms, phenyl, substituted phenyl (substitution selected from mono-lower alkyl of 1 to 3 carbon atoms, trifluoromethyl, nitro, O-alkyl of 1 to 3 carbon atoms), —$OR^7$, benzyloxy, —$NH_2$, —$NHR^7$, —$NR^7R^8$; $R^7$ is lower alkyl of 1 to 4 carbon atoms; $R^8$ is lower alkyl of 1 to 4 carbon atoms, phenyl and the pharmaceutically acceptable salts thereof;

(B) with reference to the moieties designated group (B) above:

$R^9$ is independently H, or straight chain lower alkyl of 1 to 4 carbon atoms;

$R^5$ is

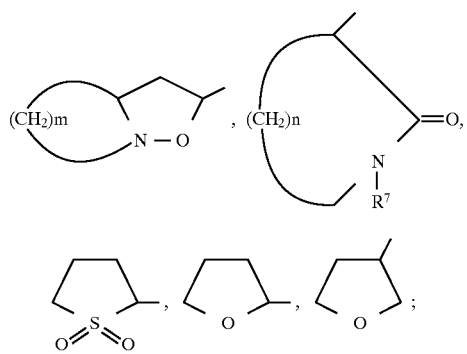

n is 2,3 or 4;

m is 3 or 4;

$R^7$ is straight chain lower alkyl of 1 to 4 carbon atoms, and the pharmaceutically acceptable salts thereof;

(C) with reference to the moieties designated group (C) above:

$R^{31}$ is H, straight chain lower alkyl of 1 to 4 carbon atoms (optionally substituted with —$OR^{17}$, —$CO_2R^{17}$, —CN, —$NH_2$, —$NHR^{17}$, —$N(R^{17})_2$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —$OR^{17}$, —$CO_2R^{17}$, —CN, —$CF_3$, —$CON(R^{17})_2$, —SPh, —$N(R^{17})_2$ or

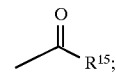

$R^{32}$ is H, straight chain lower alkyl of 1 to 4 carbon atoms (optionally substituted with —$OR^{17}$, —$CO_2R^{17}$, —CN, —$NH_2$, —$NHR^{17}$, —$N(R^{17})_2$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —$CO_2R^{17}$, —CN, —CON$(R^{17})_2$ or

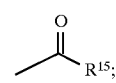

$R^{33}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene or furan, —$CO_2R^{17}$, —$CON(R^{17})_2$, —CN, —$NO_2$, or

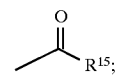

$R^{40}$ is H, $-CO_2R^{17}$, $-SO_2R^{12}$, lower alkyl of 1 to 4 carbon atoms, benzyl, substituted benzyl (substitution selected from mono-lower alkyl of 1 to 3 carbon atoms, trifluoromethyl, nitro, O-alkyl of 1 to 3 carbon atoms, F, Cl, or Br) phenyl, substituted phenyl (substitution selected from mono-lower alkyl of 1 to 3 carbon atoms, trifluoromethyl, nitro, O-alkyl of 1 to 3 carbon atoms, F, Cl, or Br), $-CON(R^{17})_2$ or

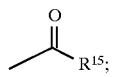

$R^{12}$ is phenyl, substituted phenyl (substitution selected from mono-lower alkyl of 1 to 3 carbon atoms, trifluoromethyl, nitro, O-alkyl of 1 to 3 carbon atoms, F, Cl, or Br);

$R^{15}$ is H, lower alkyl of 1 to 4 carbon atoms;

$R^{17}$ is independently H, or straight or branched chain lower alkyl of 1 to 4 carbon atoms;

$R^{38}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F Cl, or Br), $-CO_2R^{17}$, $-CH_2OH$, $-CN$, $-CON(R^{17})_2$ or

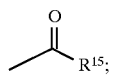

$R^{39}$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br);

$R^{10}$ is independently H, straight chain lower alkyl of 1 to 4 carbon atoms (optionally substituted with $-OR^{17}$ $-CO_2R^{17}$, $-CN$, $-NH_2$, $-NHR^{17}$, or $-N(R^{17})_2$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, $-OR^{17}$, $-CO_2R^{17}$, $-CN$, $-CF_3$, $-CON(R^{17})_2$ or

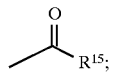

Q is a single bond, $-(CR^{10}R^{10})_{\overline{p}}$ or O;
$Q^1$ is a single bond, $-(CR^{10}R^{10})_{\overline{p}}$, O,

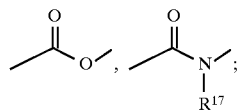

p is 1 to 5;
A is $-(CR^{10}R^{10})_q-$;
q is 2 to 5, provided that p+q is not greater than 6, and pharmaceutically acceptable salts;
(D) with reference to the moieties designated group (D) above:

$R^{41}$ is H, straight chain lower alkyl of 1 to 4 carbon atoms, $-CF_3$, $-CN$,

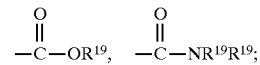

phenyl, substituted phenyl (substitution selection from mono-lower alkyl of 1 to 3 carbon atoms, $-CF_3$, nitro, O-alkyl of 1 to 3 carbon atoms), pyridine, thiophene or furan;
$R^{43}$ is $-CO_2R^{19}$,

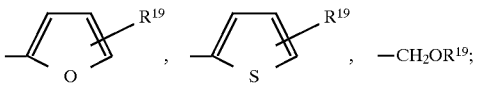

phenyl, substituted phenyl (substitution selection from mono-lower alkyl of 1 to 3 carbon atoms, $-CF_3$, nitro, O-alkyl of 1 to 3 carbon atoms), pyridine, CN, alkyl($C_1$-$C_6$) straight or branched,

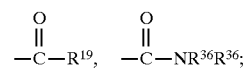

$R^{36}$ is H, straight chain or branched lower alkyl of 1 to 4 carbon atoms;

$R^{14}$ and $R^{16}$ are hydrogen, straight or branched chain lower alkyl of 1 to 4 carbon atoms, $-CO_2R^{19}$, $-CN$, phenyl, substituted phenyl (substitution selected from mono-lower alkyl of 1 to 3 carbon atoms, $-CF_3$, nitro, O-alkyl of 1 to 3 carbon atoms), pyridine, thiophene or furan,

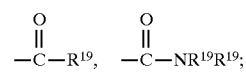

$R^{19}$ is straight or branched chain lower alkyl of 1 to 4 carbon atoms, and pharmaceutically acceptable salts;

(E) with reference to the moieties designated group (E) above:

$R^{21}$, $R^{29}$ and $R^{25}$ can be the same or different; $R^{21}$ is H, straight or branched alkyl of 1 to 4 carbon atoms, phenyl, substituted phenyl (substitution selected from mono-lower alkyl of 1 to 4 carbon atoms, $-CF_3$, nitro, $-NH_2$, O-alkyl of 1 to 4 carbon atoms, F, Cl, Br), pyridine, thiophene or furan;

$R^{29}$ is H, straight chain lower alkyl of 1 to 4 carbon atoms, phenyl, substituted phenyl (substitution selected from mono-lower alkyl of 1 to 4 carbon atoms, $-CF_3$, nitro, $-NH_2$, O-alkyl of 1 to 4 carbon atoms, F, Cl, Br), pyridine, thiophene or furan;

$R^{28}$ is phenyl, substituted phenyl (substitution selected from mono-lower alkyl of 1 to 4 carbon atoms, $-CF_3$, F, Cl, Br, nitro, O-alkyl of 1 to 4 carbon atoms);

$R^{25}$ is straight chain lower alkyl of 1 to 4 carbon atoms, phenyl, substituted phenyl (substitution selected from mono-lower alkyl of 1 to 4 carbon atoms, $-CF_3$, nitro, O-alkyl of 1 to 4 carbon atoms, F, Cl, Br), pyridine, thiophene or furan;

v is 0 to 3, and pharmaceutically acceptable salts:
(F) with reference to the moieties designated group (F) above:

A is $-(CH_2)_u$;

u is 1, 2, 3 or 4;

W is —CH$_2$— or

or A and W are each

and are connected by a —(CH$_2$)$_r$— bridge, wherein r is 1, 2 or 3;

Q is —O—, —CH$_2$— or

D is —(CH$_2$)$_f$;

f is 3 or 4;

R$^{18}$ is H, lower alkyl of 1 to 4 carbon atoms (optionally substituted with —OR$^{35}$, —CO$_2$R$^{35}$, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridine, thiophene, furan, CHO, CO$_2$R$^{35}$, —CN,

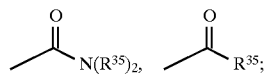

R$^{27}$ is H, straight chain lower alkyl of 1 to 4 carbon atoms (optionally substituted with OR$^{35}$, —CO$_2$R$^{35}$, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridine, thiophene or furan, —CO$_2$R$^{35}$ CHO, CO$_2$R$^{35}$, —CN, or

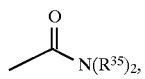

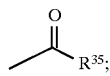

R$^{37}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene or furan, —O—R$^{35}$, —N(R$^{35}$)$_2$, —CO$_2$R$^{35}$, —CH$_2$OR$^{35}$, —CN, —CHO

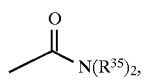

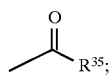

R$^{35}$ is independently H, lower alkyl of 1 to 4 carbon atoms;

R$^{13}$ is H, straight chain lower alkyl of 1 to 4 carbon atoms, cycloalkyl of 5 or 6 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene or furan, benzyl, substituted benzyl (substitution selected from mono-lower alkyl of 1 to 3 carbon atoms, trifluoromethyl, nitro, O-alkyl of 1 to 3 carbon atoms, F, Cl, or Br), —CO$_2$R$^{35}$, —SO$_2$R$^{30}$

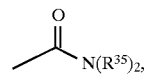

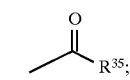

R$^{27}$ is H, straight or branched chain lower alkyl of 1 to 4 carbon atoms;

R$^{34}$ is H, —CO$_2$R$^{35}$, —SO$_2$R$^{30}$

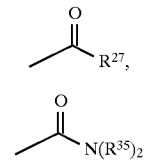

R$^{30}$ is straight or branched chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), and pharmaceutically acceptable salts:

(G) with reference to the moieties designated (G) above:

R$^{42}$ is H, straight chain lower alkyl of 1 to 4 carbon atoms, —CF$_3$, —CN,

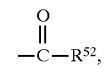

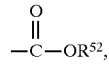

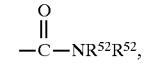

phenyl, substituted phenyl (substitution selection from mono-lower alkyl of 1 to 3 carbon atoms, —CF$_3$, nitro, O-alkyl of 1 to 3 carbon atoms), pyridine, thiophene or furan;

R$^{44}$ is straight or branched chain lower alkyl of 1 to 4 carbon atoms, cycloalkyl (rings of 3 to 8 carbon atoms), phenyl, substituted phenyl (substitution selected from mono-lower alkyl of 1 to 3 carbon atoms, —CF$_3$, nitro, O-alkyl of 1 to 3 carbon atoms), pyridine, thiophene, furan, benzyl, substituted benzyl(substitution selected from mono-lower alkyl of 1 to 3 carbon atoms, —CF$_3$, nitro, O-alkyl of 1 to 3 carbon atoms);

R$^{45}$ is H, straight or branched chain lower alkyl of 1 to 4 carbon atoms, phenyl, substituted phenyl (substitution selected from mono-lower alkyl of 1 to 3 carbon atoms, —CF$_3$, nitro, O-alkyl of 1 to 3 carbon atoms), pyridine, thiophene, furan, —CHO, —CO$_2$R$^{53}$, —OR$^{53}$ or

R⁴⁶ is H, straight or branched chain lower alkyl of 1 to 4 carbon atoms, phenyl, substituted phenyl (substitution selected from mono-lower alkyl of 1 to 3 carbon atoms, —CF₃, nitro, O-alkyl of 1 to 3 carbon atoms), pyridine, thiophene, furan, —CHO, —OR⁵³, —CO₂R⁵³ or

R⁵² is hydrogen, straight chain or branched lower alkyl of 1 to 4 carbon atoms;

R⁴⁷ is H, straight or branched chain lower alkyl of 1 to 4 carbon atoms, phenyl, substituted phenyl (substitution selected from mono-lower alkyl of 1 to 3 carbon atoms, —CF₃, nitro, O-alkyl of 1 to 3 carbon atoms), pyridine, thiophene or furan;

R⁴⁸ is H, straight or branched chain lower alkyl of 1 to 4 carbon atoms, —CF₃, phenyl, substituted phenyl (substitution selected from mono-lower alkyl of 1 to 3 carbon atoms, —CF₃, nitro, O-alkyl of 1 to 3 carbon atoms), pyridine, thiophene, furan, benzyl, subsituted benzyl(substitution selected from mono-lower alkyl of 1 to 3 carbon atoms, —CF₃, nitro, O-alkyl of 1 to 3 carbon atoms), —OR⁵², O-phenyl, O-substituted phenyl(substitution selected from mono-lower alkyl of 1 to 3 carbon atoms, —CF₃, nitro, O-alkyl of 1 to 3 carbon atoms), O-pyridine, O-thiophene, O-furan, —NH₂, —NHR⁵³, —NR⁵³R⁵³, —CO₂R⁵³, or —CONR⁵²R⁵²;

R⁴⁹ is H, straight or branched chain lower alkyl of 1 to 4 carbon atoms, —CF₃, phenyl, substituted phenyl (substitution selected from mono-lower alkyl of 1 to 3 carbon atoms, —CF₃, nitro, O-alkyl of 1 to 3 carbon atoms), pyridine, thiophene, furan, benzyl, substituted benzyl(substitution selected from monolower alkyl of 1 to 3 carbon atoms, —CF₃, nitro, O-alkyl of 1 to 3 carbon atoms), —OR⁵², O-phenyl, O-substituted phenyl(substitution selected from mono lower alkyl of 1 to 3 carbon atoms, —CF₃, nitro, O— alkyl of 1 to 3 carbon atoms), O-pyridine, O-thiophene, O-furan, —NH₂, —NHR⁵³, —NR⁵³R⁵³, —CO₂R⁵³, or —CONR⁵²R⁵².

R⁵⁰ is H, straight or branched chain lower alkyl of 1 to 4 carbon atoms, —CF₃, phenyl, substituted phenyl (substitution selected from mono-lower alkyl of 1 to 3 carbon atoms, —CF₃, nitro, O-alkyl of 1 to 3 carbon atoms), pyridine, thiophene, furan, benzyl, substituted benzyl(substitution selected from mono-lower alkyl of 1 to 3 carbon atoms, —CF₃, nitro, O-alkyl of 1 to 3 carbon atoms, —OR⁵², O-phenyl, O-substituted phenyl (substitution selected from mono-lower alkyl of 1 to 3 carbon atoms, —CF₃, nitro, O-alkyl of 1 to 3 carbon atoms), O-pyridine, O-thiophene, O-furan, —NH₂, —NHR⁵³, —NR⁵³R⁵³, —CO₂R⁵³, or —CONR⁵²R⁵²;

R⁵³ is straight or branched chain lower alkyl of 1 to 4 carbon atoms;

R⁵¹ is —CHO, —OR⁵³, —CO₂R⁵³ or

and pharmaceutically acceptable salts;

(H) with reference to the moieties designated group (H) above:

s is 1 or 2;

R⁵⁴ is straight chain lower alkyl of 1 to 4 carbon atoms (optionally substituted with —OR⁵⁶, —CO₂R⁵⁶, —CN, phenyl, substituted phenyl (substitution selected from mono-lower alkyl of 1 to 3 carbon atoms, trifluoromethyl, nitro, O-alkyl of 1 to 3 carbon atoms, trifluoromethyl, nitro, O-alkyl of 1 to 3 carbon atoms, F, Cl, Br)), phenyl, substituted phenyl (substitution selected from mono-lower alkyl of 1 to 3 carbon atoms, trifluoromethyl, nitro, O-alkyl of 1 to 3 carbon atoms, F, Cl, Br), —CN, —CO₂R⁵⁶, —CHO, —CON(R⁵⁶)₂, Br, thiophene (optionally substituted with straight chain lower alkyl of 1 to 4 carbon atoms), furan (optionally substituted with straight chain lower alkyl of 1 to 4 carbon atoms);

R⁵⁵ is H, straight chain lower alkyl of 1 to 4 carbon atoms (optionally substituted with —OR⁵⁶, —CO₂R⁵⁶, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), benzyl, substituted benzyl (substitution selected from mono-lower alkyl of 1 to 3 carbon atoms, trifluoromethyl, nitro, O-alkyl of 1 to 3 carbon atoms, F, Cl, Br), —CO₂R⁵⁶, —SO₂R⁵⁸,

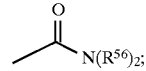

R⁵⁶ is independently H, or straight chain lower alkyl of 1 to 4 carbon atoms;

R⁵⁷ is H, straight chain lower alkyl of 1 to 4 carbon atoms;

R⁵⁸ is phenyl, substituted phenyl (substitution selected from mono-lower alkyl of 1 to 3 carbon atoms, trifluoromethyl, nitro, O-alkyl of 1 to 3 carbon atoms, trifluoromethyl, nitro, O-alkyl of 1 to 3 carbon atoms, F, Cl, Br)), benzyl, substituted benzyl (substitution selected from mono-lower alkyl of 1 to 3 carbon atoms, trifluoromethyl, nitro, O-alkyl of 1 to 3 carbon atoms, F, Cl, Br), and pharmaceutically acceptable salts;

(I) with reference to the moieties designated group (I) above:

R²⁰ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R²⁴ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R²² is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{23}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

t is 1 or 2, and pharmaceutically acceptable salts;

(J) with reference to the moieties designated group (J) above:

$R^{60}$ is H, straight chain lower alkyl of 1 to 4 carbon atoms, phenyl, substituted phenyl(substitution selected from mono-lower alkyl of 1 to 3 carbon atoms, —$CF_3$, nitro, O-alkyl of 1 to 3 carbon atoms, OR, —$NH_2$), pyridine, thiophene, or furan;

$R^{61}$ is H, straight chain lower alkyl of 1 to 4 carbon atoms, phenyl, substituted phenyl (substitution selected from mono-lower alkyl of 1 to 3 carbon atoms, —$CF_3$, nitro, O-alkyl of 1 to 3 carbon atoms, OR, —$NH_2$), pyridine, thiophene, or furan; provided, however, that $R^{60}$ and $R^{61}$ cannot be H;

$R^{62}$ is H, straight chain or branched lower alkyl of 1 to 4 carbon atoms;

$R^{63}$ is straight chain lower alkyl of 1 to 4 carbon atoms, phenyl, substituted phenyl (substitution selected from mono-lower alkyl of 1 to 3 carbon atoms, —$CF_3$, nitro, O-alkyl of 1 to 3 carbon atoms, OR, —$NH_2$), pyridine, thiophene, or furan;

$R^{64}$ is straight or branched lower alkyl of 1 to 4 carbon atoms;

w is 1 to 3, and pharmaceutically acceptable salts.

Pharmaceutically acceptable salts include both the metallic (inorganic) salts and organic salts; a list of which is given in *Remington's Pharmaceutical Sciences,* 17th Edition, pg. 1418 (1985).

DETAILED DESCRIPTION

Figure 1:
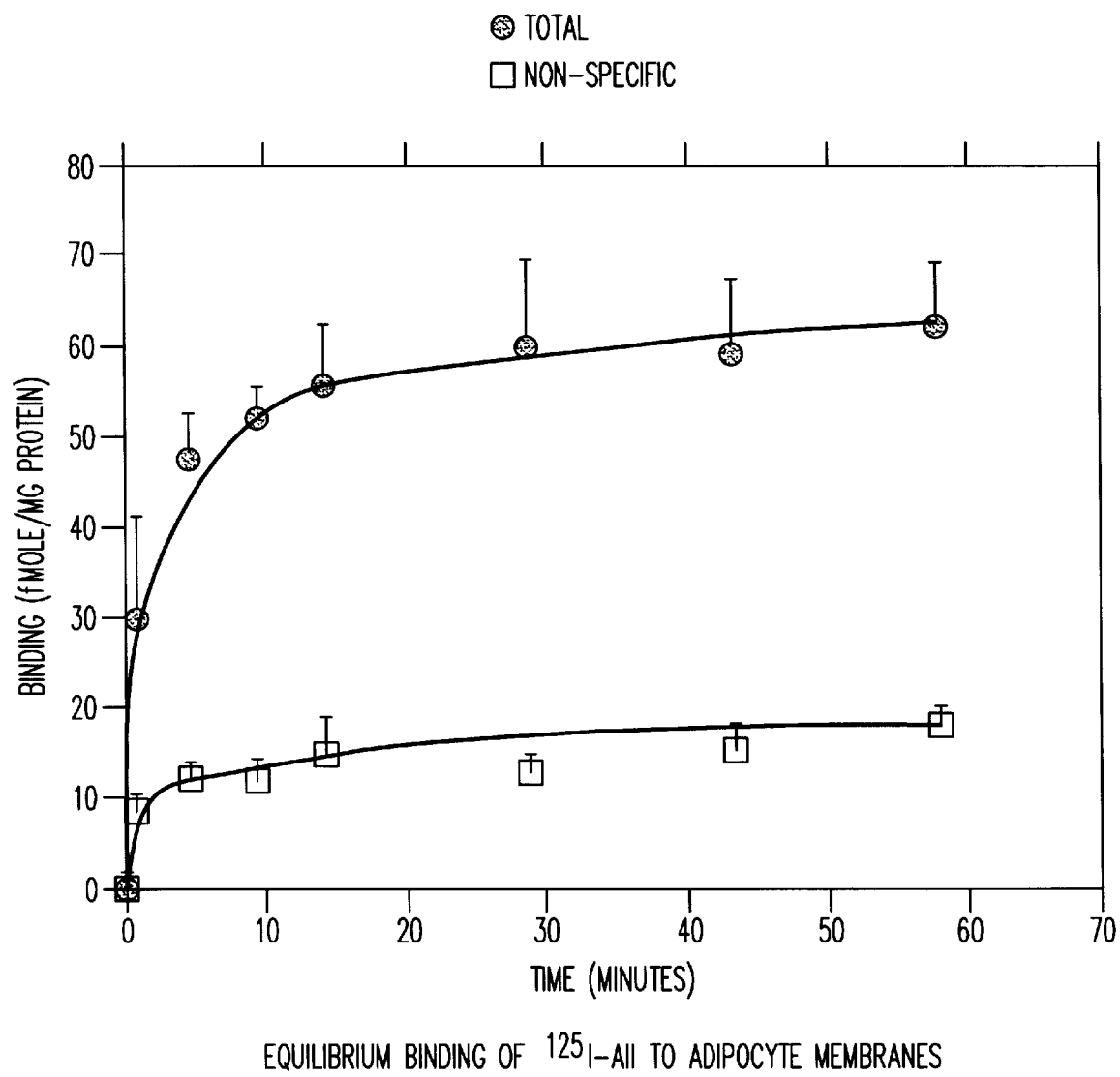
FIG. 1 shows the time course of $^{125}$I-AII association to epididymal adipocyte membranes.

Adipose tissue possesses considerable growth potential, and has recently been described as a significant source of angiotensinogen, a precursor molecule for the growth promoting decapeptide angiotensin II. To determine whether angiotensin antagonists are involved in adipose tissue expansion, both in vitro and in vivo assays are performed.

For in vitro testing, angiotensin II receptor binding assays are performed in rat adipocytes at different stages of growth. Fat cells are isolated by collagenase digestion, and plasma membranes prepared from either the epididymal or retroperitoneal fat depots of animals 40, 70 or 100 days of age. While epididymal depot weight is initially greater than retroperitoneal, during the course of the study epididymal mass increased 15 fold while retroperitoneal mass increased 25-fold. Morphologic analysis indicates that retroperitoneal adipocytes have greater volume at each age examined, and comparative differences to epididymal increased with age. Binding of $^{125}$I-[Sar$^1$,Ile$^8$]AII is rapid, saturable and specific in membranes for each site, identifying a receptor with a similar affinity of approximately 1.5 nM in both depots, and at all ages examined. Significant differences in Bmax are observed, however, which varied with the depot and the age of the animal. Epididymal fat cell membranes exhibit consistently greater numbers of AII receptors when compared to retroperitoneal adipocytes when data is expressed as binding per unit of membrane protein. The number of receptor sites per cell remain constant in retroperitoneal adipocytes at each age, which is significantly less than epididymal as cells enlarge. Relative inhibitory constants for several peptide and non-peptide AII antagonists indicate significant differences between epididymal and retroperitoneal fat cells. These data indicate significant differences in several AII binding parameters in anatomically distinct adipose tissue depots exhibiting different patterns of growth.

Measurement of the rate of association of $^{125}$I-AII to its binding site is used to calculate the time period required to achieve equilibrium. Approximately 35 µg membrane protein in 80 µL of diluted sample is placed in 96-well plates containing 10 µL BSA buffer or unlabeled AII (10 µmol/L) and 10 µL 1.0 mmol/L $^{125}$I-AII (300,000 cpm). The samples are then incubated at 22° C. for varying time periods (1, 5, 10, 15, 30, 45, and 60 minutes) in a shaking water bath. At the appropriate times, the incubations are terminated by placing the tubes in an ice bath. Each plate is then filtered according to the procedure used for the Scatchard analysis. Filters are placed into 12×75-mm glass tubes and radioactivity is measured.

The dissociation of bound $^{125}$I-AII is measured by incubating 80 µL (35 µg) freshly prepared adipocyte membranes and 10 µL $^{125}$I-AII (1.0 nmol/L, 300,000 cpm) for 30 minutes at 22° C. in a shaking water bath. At the end of the preincubation period, 10 µL unlabeled AII (10 µmol/L) is added and the membranes are subjected to a second incubation at 22° C. with gentle shaking for increasing time periods (15, 30, 75, 90, and 120 minutes). At the appropriate time intervals, plates are removed and filtered with cold 0.9% saline as previously described. Percent of binding is calculated as counts per minute of radioactivity at the aforementioned time intervals divided by the amount bound before the addition of unlabeled AII.

Binding of $^{125}$I-AII to adipocyte membranes is saturable, reversible, and displaced by known agonists and antagonists. At 22° C., binding is rapid, reaching equilibrium in approximately 15 minutes, and remained stable throughout 1 hour (FIG. 1). Temperature dependency is assessed by determining binding in three preparations at 37° C., during which specific binding reaches equilibrium in 7 to 10 minutes, a faster rate than that observed at 22° C. Linearity of the binding to increasing amounts of membrane protein is assessed by determining specific binding between 5 and 50 µg protein at 5 µg intervals. Specific binding is linear in this range, and the midpoint of 25 to 35 µg is chosen to perform all subsequent binding experiments.

Specific binding of $^{125}$I-AII to fat cell membranes is greater than 90% of total binding. At 1 nmol/L, approximately 0.5% of total radioactivity added is bound to the membrane preparation following a 30 minute incubation and filtering. Tissue-free blanks are always incubated in parallel with the membrane to determine nonspecific binding to the filter. With the Durapore filters used in these experiments, nonspecific radioactivity is 15%±1% following incubation and six rinsings each with 200 μL cold saline; additional rinsing does not decrease nonspecific filter binding below this value. Together, nonspecific filter and nonspecific fat cell membrane binding in the presence of 10 μmol/L AII accounts for approximately 20% of total binding.

Figure 2:
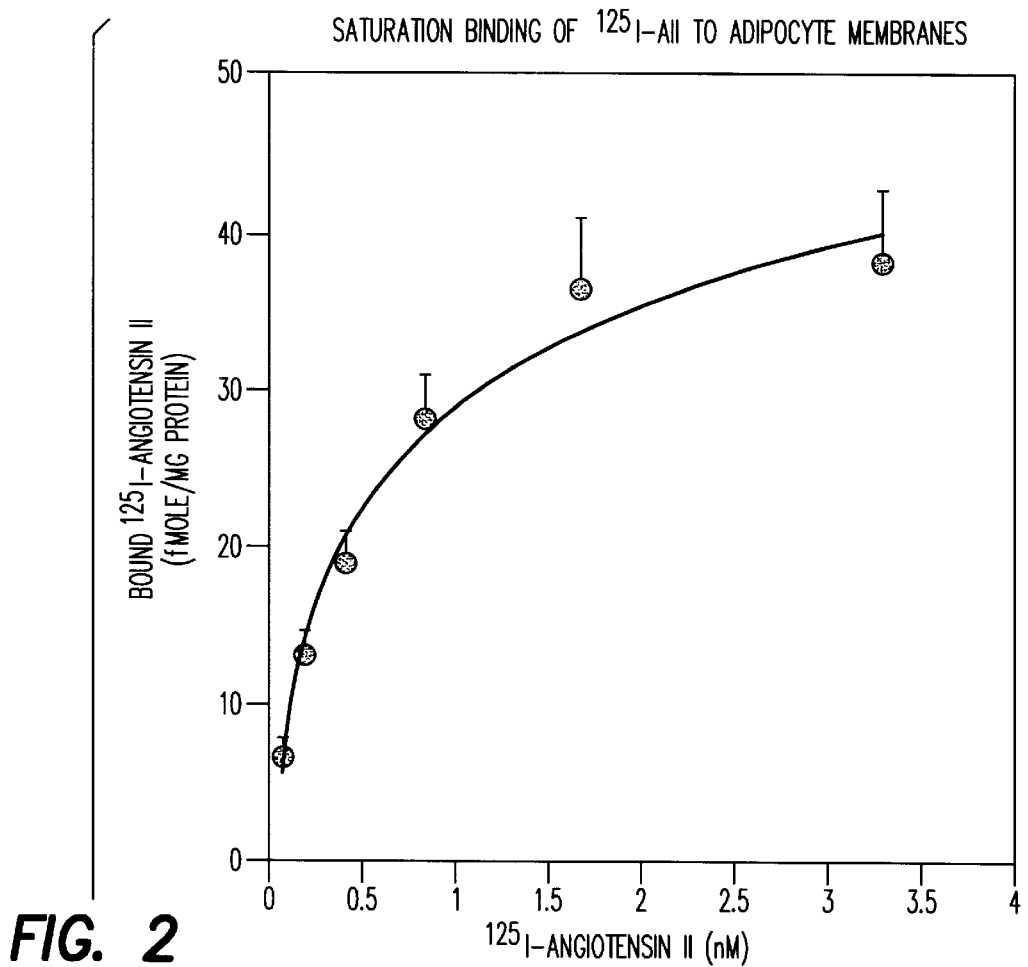
FIG. 2 shows the saturation of $^{125}$I-AII binding to adipocyte membranes.
Figure 2:
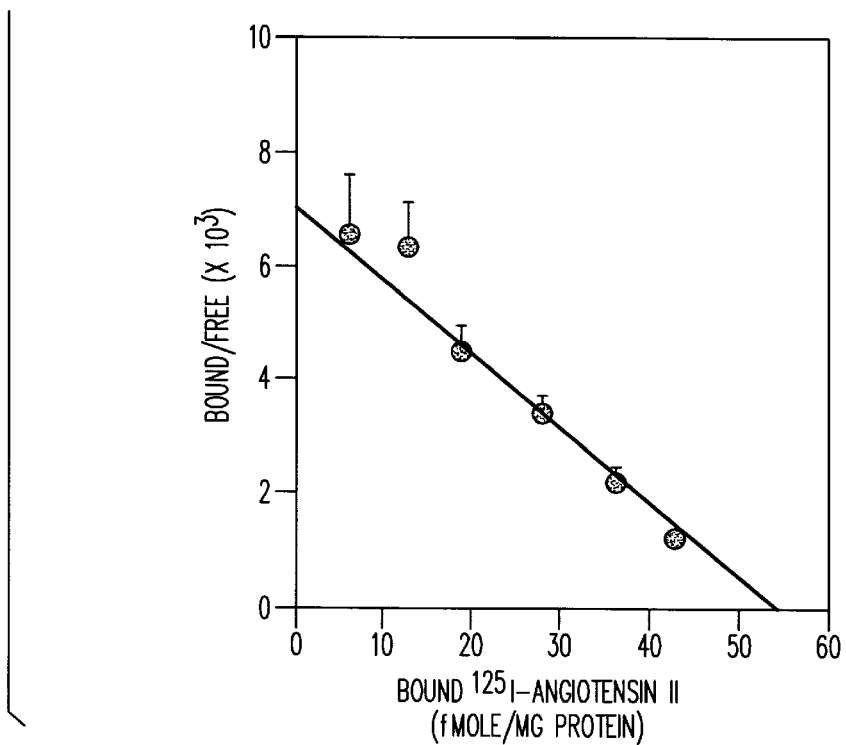
Figure 3:
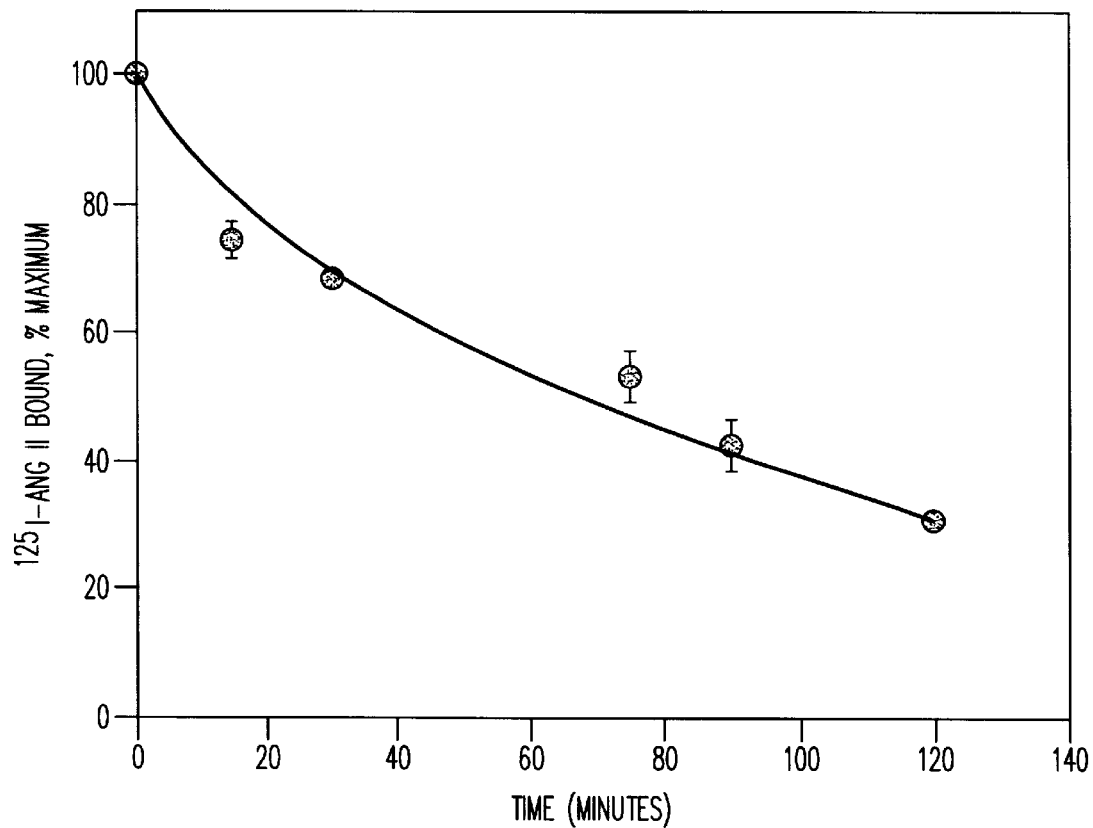
FIG. 3 shows the dissociation of $^{125}$I-AII binding from adipocyte membranes following preincubation with radiolabeled AII and addition of 10 µmol/L unlabeled AII at time=0.

Saturation of the AII receptor is shown in FIG. 2. Using equivalent quantities of membrane protein, saturation is reached at 3.5 nmol/L. Scatchard analysis of specific binding in the presence of 10 μmol/L unlabeled AII indicated a $B_{max}$ of 53.7±10.1 fmol/mg protein for epididymal adipocyte membranes; the $K_d$ value is 0.90±0.21 nmol/L. The plasma membrane-bound enzyme, 5'-nucleotidase, is also identified in the membrane preparation at a concentration of 2.01±0.24 U/μg protein. Dissociation of $^{125}$I-AII is shown in FIG. 3; approximately 50% dissociation is attained within 40 minutes and continued dissociation occurs throughout the chosen time periods.

The experimental design for determining AII binding characteristics in adipocyte membranes from growing rats is shown in Table 1. Three different groups of rats are used exhibiting different ages, body weights and fat depot weights. Body weights are significantly different between groups. When comparing individual paired depot weights between small and large rats, epididymal weight increased from 0.82 g to 12.55 g (15×), and retroperitoneal weight increased from 0.57 to 13.72 g (25×). Table 2 contains the cellular composition of the two adipose tissue depots, indicating that at each stage of growth, retroperitoneal fat cells are significantly larger in volume than the epididymal cells, although the quantitative mean difference in the small rats is less than 20 pl. As the adipocytes enlarge the number of cells per mg of membrane protein necessarily decrease.

Results of Scatchard analysis for identification of the number and affinity of AII binding sites on fat cell membranes is shown in Table 3, indicating similar affinities for all 6 groups. Significant differences are observed in $B_{max}$, however, and the pattern of binding varied between depots. When expressed as fmole/mg protein, epididymal adipocytes exhibited a similar $B_{max}$ in small and medium rats, which is significantly decreased in the older animals. A similar pattern is observed in retroperitoneal depots, suggesting an age associated decrease in receptor concentration in both sites. When comparing interdepot differences in rats of the same age, significant differences in binding is also apparent. Statistically significant differences are apparent when comparing the $B_{max}$ between retroperitoneal and epididymal adipocytes for each age. Without exception, the retroperitoneal fat cells exhibit fewer receptor sites at every age examined, even in 40 day old rats (Table 4).

Because the adipocytes are actively increasing in cell volume and number, the binding data is corrected for cell size, allowing estimation of binding sites per cell. Using this unit of expression, epididymal fat cell binding increases significantly at 70 days of age to approximately 6400 receptor sites per cell. Conversely, retroperitoneal cells exhibit minimal variability in the number of receptor sites, regardless of age or cell size. Again, retroperitoneal fat cells have significantly fewer binding sites for AII than the epididymal cells at 70 and 100 days of age.

Relative affinities of the membrane receptors for different peptide and non-peptide antagonists is shown in Table 5. For both depots, the rank order of potency for the antagonists assayed is [Sar$^1$,Ala$^8$]AII>2-n-butyl-4-chloro-5-hydroxymethyl-1-[(2'-(1H-tetrazol-5-yl)biphenyl-4-yl)methyl]imidazole>((S)-)-[[4-(di-methylamino)-3-methylphenyl]methyl-5-(diphenylacetyl)-4,5,6,7-tetrahydro-1H-imidazo[4,5-c]-pyridine-6-carboxylic acid.

TABLE 1

Rat Morphology

| Group | Body Weight | Age (days) | #Rats/ Prep | Total Depot Weight | |
|---|---|---|---|---|---|
| | | | | Epididymal | Retroperitoneal |
| Small | 149[a] | 40 | 12 | 9.75 | 6.78 |
| | ±6 | | | ±0.94 | ±0.20 |
| Medium | 390[a] | 70 | 3 | 7.75 | 7.71 |
| | ±11 | | | ±0.40 | ±0.65 |
| Large | 620[a] | 100 | 1 | 12.55 | 13.72 |
| | ±17 | | | ±1.62 | ±3.07 |

*Depot weight per animal is equivalent to total weight divided by the number of rats/preparation
[a]Significantly different from other group body weights at $p < 0.001$

TABLE 2

Adipocyte Morphology

| CELL SIZE | Epididymal | | | Retroperitoneal | | |
|---|---|---|---|---|---|---|
| | Cell Diameter (μm) | Cell Volume (pl) | Cells/mg[a] membrane protein | Cell Diameter (μm) | Cell Volume (pl) | Cells/mg[a] membrane protein |
| Small | 50.0 | 82 | 7.78 | 51.9 | 98* | 6.84 |
| | ±0.8 | ±4 | ±0.44 | ±0.2 | ±4 | ±0.48 |
| Medium | 67.8 | 192 | 4.49 | 75.7* | 276* | 3.72 |
| | ±1.7 | ±13 | ±0.33 | ±1.8 | ±20 | ±0.30 |
| Large | 95.1 | 508 | 2.76 | 98.3 | 603* | 2.63 |
| | ±5.2 | ±80 | ±0.50 | ±4.0 | ±68 | ±0.26 |

*Significantly greater than epididymal value at $p < 0.01$.
No significant differences between cells/mg protein for epididymal vs. retroperitoneal at any size.
[a]Values represent cells × 10$^6$. Cell volume, diameter, and membrane protein values are always significantly different ($p < 0.01$) from the next age group within each depot.

TABLE 3

Scatchard Analysis of Fat Cell Membranes

| CELL SIZE | Epididymal | | Retroperitoneal | |
|---|---|---|---|---|
| | $B_{max}$ (fmole/ mg protein) | $K_D$ (nM) | $B_{max}$ (fmole/ mg protein) | $K_D$ (nM) |
| Small | 46.4 | 1.44 | 30.0* | 1.84 |
| | (6.8) | (0.20) | (4.6) | (0.31) |
| | n = 8 | | n = 8 | |
| Medium | 57.2 | 1.73 | 24.6* | 1.82 |
| | (7.2) | (0.65) | (7.1) | (0.71) |
| | n = 5 | | n = 5 | |
| Large | 26.0[a] | 1.68 | 11.2[b],* | 1.76 |
| | (3.9) | (0.26) | (3.2) | (0.51) |
| | n = 3 | | n = 3 | |

[a]Significantly different from medium sized epididymal membranes at $p < 0.05$
[b]Significantly different from small and medium sized retroperitoneal membranes at $p < 0.05$
*Significantly different from corresponding epididymal value at $p < 0.05$
All values are mean with SEM in parenthesis of "n" experiments

TABLE 4

Angiotensin Receptor Sites Per Cell

| Cell Size | Epididymal (E) | Retroperitoneal (R) |
|---|---|---|
| Small (S) | 2695 | 2493 |
|  | ±392 | ±378 |
| Medium (M) | 6379[a] | 3371* |
|  | ±195 | ±881 |
| Large (L) | 5672[a] | 2561* |
|  | ±845 | ±730 |

[a]Significantly different from small epididymal membranes (ES) at $p < 0.005$
*Significantly different from corresponding epididymal value at $p < 0.05$

TABLE 5

Inhibitory Constants ($IC_{50}$) of Ligands for Displacement of $^{125}I[Sar,Ile]$ AII Binding in Rat Fat Cell Membranes

| Compound | Epididymal | Retroperitoneal |
|---|---|---|
| ** | $1.09 \times 10^{-8}$ M | $7.36 \times 10^{-9}$ M |
|  | (0.32) | (2.17) |
| Sar$^1$-Ala$^8$AII | $4.31 \times 10^{-9}$ M | $2.63 \times 10^{-9}$ M |
|  | (0.61) | (0.26) |
| *** | $1.73 \times 10^{-4}$ M | $2.42 \times 10^{-4}$ M |
|  | (0.23) | (0.36) |
| AII | $3.34 \times 10^{-9}$ M | $3.71 \times 10^{-9}$ M |
|  | (0.25) | (0.45) |
| AIII | $2.23 \times 10^{-8}$ M | $1.85 \times 10^{-8}$ M |
|  | (0.69) | (0.43) |
| Sar$^1$-Leu$^8$ AII | $4.41 \times 10^{-9}$ M | $2.66 \times 10^{-9}$ M |
|  | (0.72) |  |

Values are calculated $IC_{50}$'s from 1-4 different assays for each treatment.

**2-n-butyl-4-chloro-5-hydroxymethyl-1-[(2'-(1H-tetrazol-5-yl)biphenyl-4-yl)-methyl]imidazole.
***((S)-)-[[4-(dimethylamino)-3-methylphenyl]methyl-5-(diphenylacetyl)-4,5,6,7-tetrahydro-1H-imidazo[4,5-c]pyridine-6-carboxylic acid.

Synthetic compounds which are known to possess angiotensin II(AII) receptor blocking activity are given to rats to determine the effects of AII antagonists on adipose tissue over a two week period. Male rats received either distilled water (control), 2-n-butyl-4-chloro-5-hydroxymethyl-1-[(2'-(1H-tetrazol-5-yl)biphenyl-4-yl)methyl]imidazole or cis-(±)-2-butyl-6-(hexahydro-2-methylpyrrolo[1,2-b]isoxazol-2-yl)-3-[[2'-(1H-tetrazol-5-yl)[1,1'-biphenyl]-4-yl]-methyl-4(3H)-quinazolinone sodium salt (15 mg/kg each) formulated in distilled water once a day by gavage. Body weight and food intake are monitored daily. At the end of two weeks, the rats are sacrificed and tissues are weighed. Adipocyte membranes are prepared by collagenase digestion, homogenization and centrfugation. The cell volume is determined by sizing the diameter of 200 adipocytes and binding to the adipocyte AII receptor is determined using a radioligand binding assay. As shown in Table 6, those rats given the AII receptor antagonists exhibited both a lower final body weight and body weight gain. Of the organs sampled, the combined largest relative and quantitative change in weight was in the adipose tissue. Table 7 indicates that rats receiving orally the AII antagonists exhibited smaller epididymal cell volume and reduced capacity for binding.

TABLE 6

In vivo Effects of AII Receptor Antagonists on Rat Body and Tissue Weights

| | Control | * | % Change From Control | ** | % Change From Control |
|---|---|---|---|---|---|
| Initial | 399 | 399 | | 396 | |
| Body Weight (g) | (9.2) | (9.2) | | (7.0) | |
| Final | 455 | 424 | -7 | 431 | -5 |
| Body Weight (g) | (11.4) | (11.5) | | (11.2) | |
| Avg. Weight | 56 | 25 | -55 | 35 | -38 |
| Gain (g) | (4.1) | (6.8) | | (6.2) | |
| Avg. Daily | 32.8 | 30.4 | -7 | 30.1 | -8 |
| Food Intake (g) | (.82) | (.92) | | (.78) | |
| Epididymal | 5.20 | 4.33 | -17 | 4.10 | -21 |
| Fat Weight (g) | (.39) | (.31) | | (.19) | |
| Retroperitoneal | 4.87 | 4.35 | -11 | 4.10 | -16 |
| Fat Weight (g) | (.42) | (.47) | | (.46) | |
| Heart Weight (g) | 1.49 | 1.41 | -5 | 1.39 | -7 |
| | (.03) | (.06) | | (.07) | |
| Liver Weight (g) | 17.5 | 15.8 | -10 | 16.5 | -6 |
| | (.74) | (1.0) | | (.49) | |
| Testes Weight (g) | 3.4 | 3.5 | +5 | 3.3 | -1 |
| | (.09) | (.13) | | (.16) | |
| Kidney Weight (g) | 3.8 | 3.5 | -7 | 3.6 | -4 |
| | (.19) | (.13) | | (.15) | |
| Spleen Weight (g) | .96 | .71 | -25 | .78 | -20 |
| | (.06) | (.05) | | (.03) | |

Values are mean with (SEM) of n = 6 rats per group.
*cis-(+/-)-2-butyl-6-(hexahydro-2-methylpyrrolo[1,2-b]-isoxazol-2-yl)-3-[[2'-(1H-tetrazol-5-yl)[1,1'-bi-phenyl]-4-yl]methyl-4(3H)-quinazolinone sodium salt.
**2-n-butyl-4-chloro-5-hydroxymethyl-1-[(2'-(1H-tetrazol-5-yl)biphenyl-4-yl)methyl]imidazole.

TABLE 7

Epididymal Adipocyte AII Receptor Binding and Adipocyte Volume

|  | Control | * | ** |
|---|---|---|---|
| $B_{max}$ (fmole/mg protein) | 48.6 (15.7) | 31.8 (8.5) | 24.7 (3.4) |
| Adipocyte Cell Volume (p1) | 256 (30.3) | 187 (22.1) | 163 (4.9) |

Values are mean (SEM) of 4 rats/group orally receiving water (Control) or an AII antagonist once daily for 2 weeks.
*cis-(+/−)-2-butyl-6-(hexahydro-2-methylpyrrolo[1,2-b]isoxazol-2-yl)-3-[[2'-(1H-tetrazol-5-yl)[1,1'-bi-phenyl]-4-yl]methyl-4(3H)-quinazolinone sodium salt.
**2-n-butyl-4-chloro-5-hydroxymethyl-1-[(2'-(1H-tetrazol-5-yl)biphenyl-4-yl)methyl]imidazole.

Method for Screening Adipocyte Membranes for Angiotensin II Receptor Binding

The experimental design involves determining the binding characteristics of adipocyte membranes harvested from two different anatomic sites at three different ages. Male Sprague-Dawley rats (Charles River Laboratories, Wilmington, Mass.) are used at 40, 70 and 100 days of age.

Rats are killed by carbon dioxide inhalation on the morning of the experiment, and adipose tissue from the epididymal and retroperitoneal depots is quickly excised and placed in cold saline. The spermatic artery and vein are removed from the epididymal fat, and brown fat deposits are dissected away from the retroperitoneal depot. The adipose tissue is weighed, minced into small pieces, and approximately 10 g each transferred to a flask containing 25 ml of Krebs-Ringer-bicarbonate buffer (KRB), 6 mM glucose and 50 mg of collagenase, pH 7.4. The flask containing the minced adipose tissue is shaken vigorously (150 strokes/min) for 30 minutes, followed by passing of the contents through 150 um nylon mesh. Intact adipocytes dissociated from the tissue pass freely into waiting tubes, while the undigested tissue is trapped on the screen. The tubes containing the adipocytes are washed an additional 4× with 20 ml each of cold Tris buffer (10 mM Tris HCl, pH 8.0) by first allowing the adipocytes to separate from the digestion medium by flotation, removing the infranatant through polyethylene tubing attached to a syringe, resuspending the cells in the Tris buffer, and repeating this procedure.

Adipocyte membranes used for binding studies are prepared as follows. Using a Brinkmann polytron with a small, blunt probe, adipocytes are homogenized for 20 second at a medium speed setting, and the resulting homogenate centrifuged at 40,000×g for 35 minutes and 4° C. Following centrifugation, the fat cake and supernatant are carefully removed, and the pellet resuspended in 1 ml of Tris buffer. Protein content of the high speed pellet is determined, the resuspended protein is either assayed immediately or stored at −75° before binding assays are performed.

Binding is initiated by suspending the adipocyte membranes in 0.25% BSA buffer (bovine serum albumin, 50 mM Tris HCl, 5 mM $MgCl_2$, pH 7.4) to a final concentration of 5 ug protein/10 ul buffer. For Scatchard analysis, membranes are incubated with 12 different concentrations of $^{125}I[Sar^1, Ile^8]AII$(NEN, Boston, Mass.) ranging from 0.15 to 5.0 nM. A typical incubation tube contains 160 ul(80 ug) fat cell membrane protein, 20 ul of isotope and 20 ul of 1 uM 2-n-butyl-4-(chloro-5-hydroxymethyl-1-[(2'-(1H-tetrazol-5-yl)biphenyl-4-yl)methyl]imidazole as appropriately required for determination of nonspecific binding. The assay is initiated by the addition of the membrane protein, followed by incubation at 22° C. for 30 minutes in a slowly shaking water bath. Separation of bound from free radioactivity is achieved using any appropriate filtration apparatus. We use either a Millipore or Brandel model harvesting apparatus containing a Durapore or Whatman GF/B filter, followed by 6 additional rinses with 5 ml each of cold saline. The filters are placed in tubes, and radioactivity measured in a gamma scintillation counter programmed to correct for the half-life of the isotope. Using this experimental protocol, both the affinity ($K_D$) and number of binding sites ($B_{max}$) for angiotensin II on the adipocyte membrane can be calculated.

The relative affinities of different anatomically distinct adipocyte membranes for a variety of peptide and nonpeptide antagonists can also be determined. Fat cell membranes are incubated in the presence of 1 $nM^{125}I$-$[Sar^1,Ile^8]AII$ together with varying concentrations of antagonists ranging from $10^{-6}$ to $10^{-13}M$, and in increasing graduations of one-third log unit. Concentration ranges can be altered dependent upon the affinity of the particular antagonist for the fat cell membrane receptor. Relative inhibitory constants required to displace 50% of bound ligand ($IC_{50's}$) are calculated based upon comparative specific binding of the radioligand in the presence of antagonists.

The inhibitory constants ($IC_{50}$) of various compounds tested for displacement of $^{125}I[Sar,Ile]AII$ binding in rat epididymal fat cell membranes is shown in Table 8.

TABLE 8

Inhibitory Constants ($IC_{50}$) of Test Compounds for Displacement of $^{125}I[Sar, Ile]AII$ Binding in Rat Epididymal Fat Cell Membranes

| Compound | Epididymal $IC_{50}$ |
|---|---|
| (3S-trans)-2-butyl-6-[5-(hydroxymethyl)-2-methyl-3-isoxazolidinyl]-3-[[2'-(1H-tetrazol-5-yl)[1,1'-biphenyl]-4-yl]methyl]-4(3H)-quinazolinone | $1.86 \times 10^{-8}$ |
| (3R-cis)-2-butyl-6-[5-(hydroxymethyl)-2-methyl-3-isoxazolidinyl]-3-[[2'-(1H-tetrazol-5-yl)[1,1'-biphenyl-4-yl]-methyl]-4(3H)-quinazolinone | $8.20 \times 10^{-9}$ |
| 2-butyl-6-(phenoxymethyl)-3-[[2'-(1H-tetrazol-5-yl)[1,1'-biphenyl]-4-yl]-methyl]-4(3H)-quinazolinone | $1.63 \times 10^{-7}$ |
| 2-butyl-6-[(2-pyridinyloxy)methyl]-3-[[2'-(1H-tetrazol-5-yl)[1,1'-biphenyl]-4-yl]methyl]-4(3H)-quinazolinone hydrochloride | $1.72 \times 10^{-8}$ |
| 2-butyl-6-(3,3a,4,5,6,7-hexahydropyrazolo[1,5-a]pyridin-2-yl)-3-[[2'-(1H-tetrazol-5-yl)[1,1'-biphenyl]-4-yl]-methyl]-4(3H)-quinazolinone | $8.67 \times 10^{-8}$ |
| (3aα,6aα)-3-[2-butyl-3,4-dihydro-4-oxo-3-[[2'-(1H-tetrazol-5-yl)[1,1'-biphenyl]-4-yl]methyl]-6-quinazolinyl]-2,3,3a,6a-tetrahydro-3,5-dimethylpyrrolo[3,4-c]pyrazole-4,6-(1H,5H)-dione | $5.50 \times 10^{-7}$ |
| 2-butyl-6-[4,5-dihydro-3-(4-methyl-phenyl)-5-isoxazolyl]-3-[[2'-(1H-tetrazol-5-yl) [1,1'-biphenyl]-4-yl] methyl]-4(3H)-quinazolinone | $1.26 \times 10^{-7}$ |
| 5-[2-butyl-3,4-dihydro-4-oxo-3-[[2'-(1H-tetrazol-5-yl) [1,1'-biphenyl]-4-yl]methyl]-6-quinazolinyl]-4,5-dihyrdro-5-methyl-3-isoxazolecarboxylic acid ethyl ester | $3.57 \times 10^{-8}$ |
| [2S-(2α,3aα,3bβ,8aα)]-2-butyl-6-(6,6'-dimethyloctahydrofuro[3,2-d]pyrrolo[1,2-d]isoxazol-2-yl)-3-[[2'-(1H- | $1.41 \times 10^{-8}$ |

TABLE 8-continued

Inhibitory Constants (IC$_{50}$) of Test Compounds for Displacement of $^{125}$I[Sar, Ile]AII Binding in Rat Epididymal Fat Cell Membranes

| Compound | Epididymal IC$_{50}$ |
|---|---|
| tetrazol-5-yl) [1,1'-biphenyl]-4-yl]-methyl]-4(3H)-quinazolinone | |
| 2-butyl-6-[hydroxy(tetrahydro-2-thienyl)methyl]-3-[[2'-(1H-tetrazol-5-yl) [1,1'-biphenyl]-4-yl]methyl]-4(3H)-quinazolinone S,S-dioxide isomer 1 | 1.68 × 10$^{-9}$ |
| 2-butyl-6-[hydroxy(tetrahydro-2-thienyl)methyl]-3-[[2'-(1H-tetrazol-5-yl) [1,1'-biphenyl]-4-yl]methyl]-4(3H)-quinazolinone S,S-dioxide isomer 2 | 3.14 × 10$^{-9}$ |
| 2-butyl-6-[1-hydroxy-1-(1-methyl-2-oxo-3-pyrrolidinyl)ethyl]-3-[[2'-(1H-tetrazol-5-yl) [1,1'-biphenyl]-4-yl]methyl]-4(3H)-quinazolinone isomer 1 | 7.90 × 10$^{-9}$ |
| trans-(+/−)-2-[2-butyl-3,4-dihydro-4-oxo-3-[[2'-(1H-tetrazol-5-yl) [1,1'-biphenyl]-4-yl]methyl]-6-quinazolinyl]-hexahydropyrrolo[1,2-b]isoxazole-2-carboxylic acid methyl ester monohydro | 2.35 × 10$^{-8}$ |
| cis-(+/−)-2-butyl-6-(hexahydro-2-methyl-pyrrolo[1,2-b]isoxazol-2-yl)-3-[[2'-(1H-tetrazol-5-yl) [1,1-biphenyl]-4-yl]-methyl]-4(3H)-quinazolinone sodium salt | 1.46 × 10$^{-8}$ |
| 2-butyl-3,5,7,8-tetrahydro-3-[[2'-(1H-tetrazol-5-yl) [1,1'-biphenyl]-4-yl]-methyl]-pyrido[4,3-d]pyrimidin-6(4H)-carboxylic acid phenylmethyl ester | 1.79 × 10$^{-8}$ |
| 2-butyl-5,6,7,8-tetrahydro-6-(2-hydroxy-2-methyl-1-oxopropyl)-3-[[2'-(1H-tetrazol-5-yl) [1,1'-biphenyl]-4-yl]-methyl]-4(3H)-quinazolinone | 1.36 × 10$^{-9}$ |
| 2-ethyl-5,7-dimethyl-3-[[2'-(1H-tetrazol-5-yl) [1,1-biphenyl]-4-yl]methyl]-3H-imidazo[4,5-b]pyridine | 2.44 × 10$^{-9}$ |
| 5-methyl-7-propyl-8-[(2'-(1H-tetrazol-5-yl)biphenyl-4-yl)methyl]-1,2,4-triazolo[1,5-c]pyrimidin-2(3H)-one | 5.63 × 10$^{-9}$ |

Additional Calculations

The number of AII receptor binding sites per cell can be estimated by initially determining the amount of membrane protein and the number of adipocytes in each preparation. This information allows an estimate of the amount of membrane protein per cell, which together with B$_{max}$ expressed as fmole/mg protein, results in calculations of sites per cell.

Human Adipocyte Membrane Preparations

Human adipose tissue is obtained from surgical biopsy and placed immediately in cold saline. Within 1 hour of receiving the sample, it is weighed and minced into small pieces and placed into a solution of Krebs's Ringer bicarbonate buffer (pH 7.4), containing 6 mM glucose and collagenase at 2 mg/ml. The tissue is shaken at 150 strokes/min at 37° C., and at 10 minute intervals the solution is passed through nylon mesh to separate the free adipocytes from the remainder of the tissue. The procedure differs from rat adipose tissue, as human cells are more fragile and require shorter periods of digestion before separation from the digestion medium. The undigested tissue is minced again before adding back to the collagenase-Krebs buffer, and digested at 10 minute intervals until completely digested. The adipocytes are rinsed with cold Tris buffer, and the procedure for membrane preparation, and determination of angiotensin II binding to the adipocyte membrane proceeds as with the rat adipocyte.

Human adipocytes exhibit displacement of $^{125}$I-Sar Ile with high affinity by the AII antagonist 2-n-butyl-4-(chloro-5-hydroxymethyl-1-[(2'-(1 H-tetrazol-5-yl)biphenyl-4-yl)methyl]imidazole (Table 9).

TABLE 9

Angiotensin II Antagonist Displacement of $^{125}$I-Sar-Isoleucine Angiotensin II in Human Adipocytes

| | Site of Adipose Tissue | |
|---|---|---|
| * | Omental (nM) | Subcutaneous (nM) |
| MEAN IC$_{50}$ | 9.26 | 16.11 |
| SEM | 3.39 | 4.51 |

*2-n-butyl-4-(chloro-5-hydroxymethyl-1-[(2'-(1H-tetrazol-5-yl)biphenyl-4-yl)methyl]imidazole.

I claim:

1. A method of reducing adipose tissue growth in a mammal comprising administering to such mammal an amount of an Angiotensin (AII) Antagonist effective to reduce the growth of adipose tissue.

2. A method of treating obesity in a mammal comprising administering to such mammal an amount of an Angiotensin (AII) Antagonist effective to reduce the growth of adipose tissue.

3. A method of treating obesity in a mammal afflicted with non-insulin dependent diabetes mellitus which comprises administering to such mammal an amount of an Angiotensin (AII) Antagonist effective to reduce the growth of adipose tissue.

4. A method according to claims 1, 2 or 3 wherein the Angiotensin (AII) Antagonist is selected from a compound of the formula:

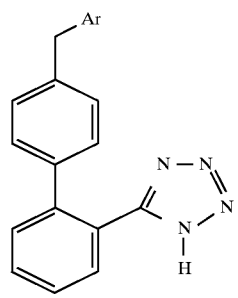

Formula 1 wherein:

Ar is selected from the group consisting of

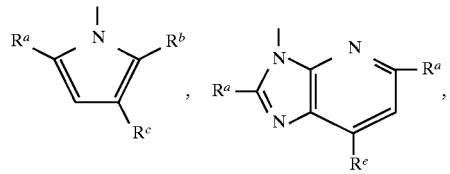

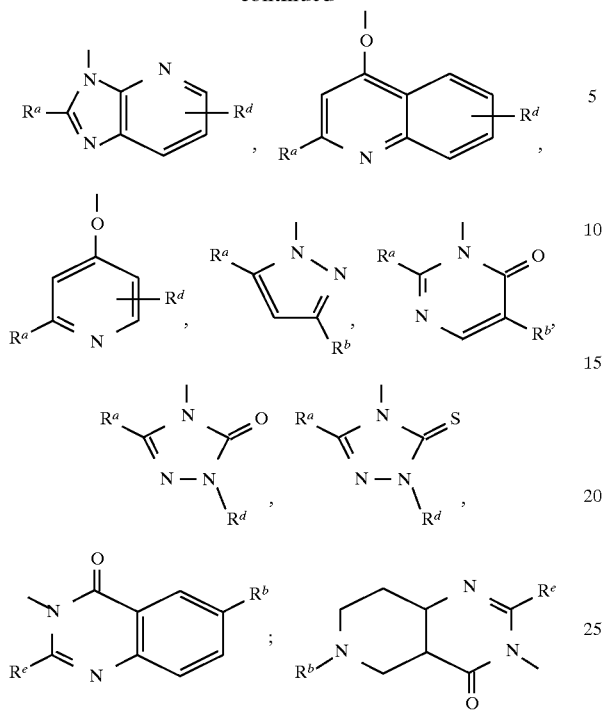

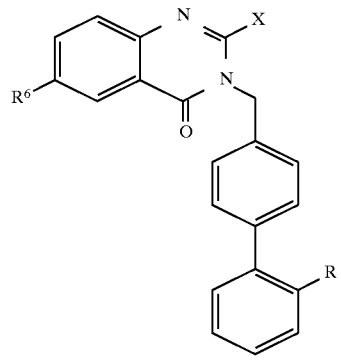

$R^a$ and $R^e$ are each independently lower alkyl of 1 to 5 carbon atoms;

$R^b$ is selected from:
  (a) (C1–C6)alkyl optionally substituted with a substituent selected from the group consisting of hydroxy, (C1–C4)alkoxy, (C1–C4)alkyl, phenyl, substituted phenyl(substituent selected from (C1–C4)alkyl, $CF_3$, nitro, $-NH_2$, (C1–C4)alkoxy and halo), pyridine, thiophene, furan, —CHO, —COORf, —O—CORf, —CORf, —CON(Rf)2, and carboxymethylphenyl;
  (b) a 5–15 membered monocyclic, bicyclic or tricyclic heterocyclic group wherein the heteroatom(s) are selected from 1–4 oxygen, sulfur or nitrogen atoms optionally substituted by (C1–C4)alkyl, (optionally substituted with —ORf, $-CO_2Rf$, —CN, $-NH_2$, —NHRf, $-N(Rf)_2$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —ORf, $-CO_2Rf$, —CN, $-CF_3$, $-CON(Rf)_2$, —SPh, $-N(Rf)_2$;

$R^c$ is hydrogen, halo or a pyrrole group attached at the nitrogen atom and unsubstituted or substituted by lower alkyl of 1 to 4 carbon atoms, Rd and Rf are independently selected from hydrogen and lower alkyl of 1 to 4 carbon atoms, a tautomer thereof and the pharmaceutically acceptable salts thereof.

5. A method according to claims 1, 2 or 3 wherein the Angiotension (AII) Antagonist is selected from a compound of the formula:

wherein:
R is $-CO_2H$, $-NHSO_2CF$ or

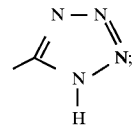

X is straight or branched alkyl of 3 to 5 carbon atoms;
$R^6$ is selected from the following moieties:

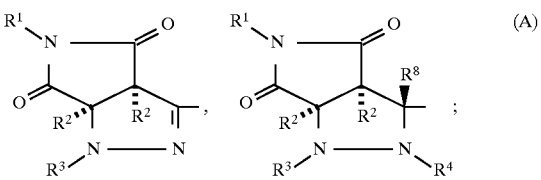

(A)

$R^1$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), 2-pyridinyl, 4-pyridinyl, benzyl, substituted benzyl (substitution selected from mono-lower alkyl of 1 to 3 carbon atoms, trifluoromethyl, nitro, O-alkyl of 1 to 3 carbon atoms);

$R^2$ is H, and straight chain lower alkyl of 1 to 4 carbon atoms;

$R^3$ is H, triphenylmethyl, benzyl, substituted benzyl (substitution selected from mono-lower alkyl of 1 to 3 carbon atoms, trifluoromethyl, nitro, O-alkyl of 1 to 3 carbon atoms), straight chain lower alkyl of 1 to 4 carbon atoms;

$R^4$ is H, straight chain lower alkyl of 1 to 4 carbon atoms,

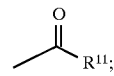

$R^{11}$ is lower alkyl of 1 to 3 carbon atoms, phenyl, substituted phenyl (substitution selected from mono-lower alkyl of 1 to 3 carbon atoms, trifluoromethyl, nitro, O-alkyl of 1 to 3 carbon atoms), $-OR^7$, benzyloxy, $-NH_2$, $-NH^7$, $-NR^7R^7$;

$R^7$ is lower alkyl of 1 to 4 carbon atoms;

$R^8$ is lower alkyl of 1 to 4 carbon atoms, phenyl; and the pharmaceutically acceptable salts thereof.

6. A method according to claims 1, 2 or 3 wherein the Angiotensin (AII) Antagonist is selected from a compound of the formula:

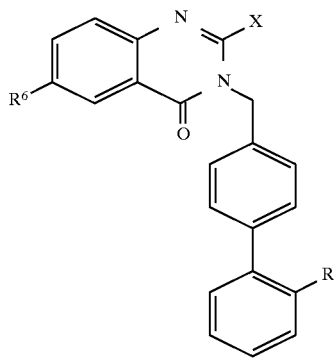

wherein:

R is —CO$_2$H, —NHSO$_2$CF$_3$ or

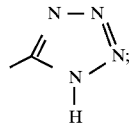

X is straight or branched alkyl of 3 to 5 carbon atoms;

R$^6$ is selected from the following moieties:

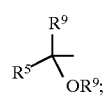 (B)

R$^9$ is independently H, or straight chain lower alkyl of 1 to 4 carbon atoms;

R$^5$ is

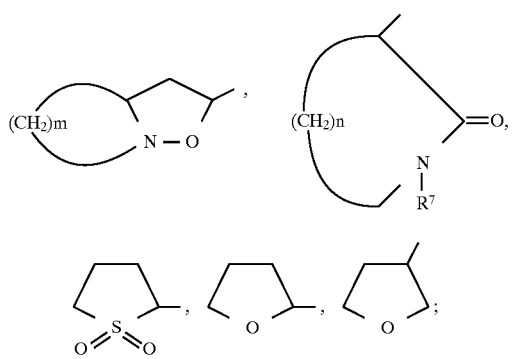

n is 2,3 or 4;

m is 3 or 4;

R$^7$ is straight chain lower alkyl of 1 to 4 carbon atoms; and the pharmaceutically acceptable salts thereof.

7. A method according to claims 1, 2 or 3 wherein the Angiotensin (AII) Antagonist is selected from a compound of the formula:

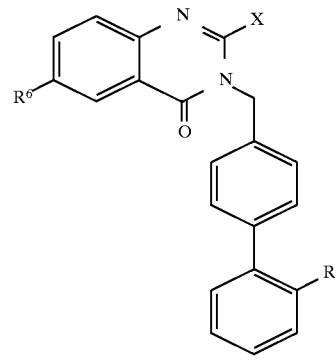

wherein:
R is —CO$_2$H, —NHSO$_2$CF$_3$ or

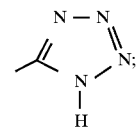

X is straight or branched alkyl of 3 to 5 carbon atoms;
R$^6$ is selected from the following moieties:

(c)

R$^{31}$ is H, straight chain lower alkyl of 1 to 4 carbon atoms (optionally substituted with —OR$^{17}$, —CO$_2$R$^{17}$, —CN, —NH$_2$, —NHR$^{17}$, —N(R$^{17}$)$_2$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —OR$^{17}$, —CO$_2$R$^{17}$, —CN, —CF$_3$, —CON(R$^{17}$)$_2$, —SPh, —N(R$^{17}$)$_2$ or $$\underset{R^{15}}{\overset{O}{\|}}$$

R$^{32}$ is H, straight chain lower alkyl of 1 to 4 carbon atoms (optionally substituted with —OR$^{17}$, —CO$_2$R$^{17}$, —CN, —NH$_2$, —NHR$^{17}$, —N(R$^{17}$)$_2$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —CO$_2$R$^{17}$, —CN, —CON(R$^{17}$)$_2$ or $$\underset{R^{15}}{\overset{O}{\|}}$$

R$^{33}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene or furan, —CO$_2$R$^{17}$, —CON(R$^{17}$)$_2$, —CN, —NO$_2$, or $$\underset{R^{15}}{\overset{O}{\|}}$$

R$^{40}$ is H, —CO$_2$R$^{17}$, —SO$_2$R$^{12}$, lower alkyl of 1 to 4 carbon atoms, benzyl, substituted benzyl (substitution selected from mono-lower alkyl of 1 to 3 carbon atoms, trifluoromethyl, nitro, O-alkyl of 1 to 3 carbon atoms, F, Cl, or Br) phenyl, substituted phenyl (substitution selected from mono-lower alkyl of 1 to 3 carbon atoms, trifluoromethyl, nitro, O-alkyl of 1 to 3 carbon atoms, F, Cl, or Br), —CON(R$^{17}$)$_2$ or $$\underset{R^{15}}{\overset{O}{\|}}$$

R$^{12}$ is phenyl, substituted phenyl (substitution selected from mono-lower alkyl of 1 to 3 carbon atoms, trifluoromethyl, nitro, O-alkyl of 1 to 3 carbon atoms, F, Cl, or Br);

R$^{15}$ is H, lower alkyl of 1 to 4 carbon atoms;

R$^{17}$ is independently H, or straight or branched chain lower alkyl of 1 to 4 carbon atoms;

R$^{38}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), —CO$_2$R$^{17}$, —CH$_2$OH, —CN, —CON(R$^{17}$)$_2$ or $$\underset{R^{15}}{\overset{O}{\|}}$$

R$^{39}$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br);

R$^{10}$ is independently H, straight chain lower alkyl of 1 to 4 carbon atoms (optionally substituted with —OR$^{17}$, —CO$_2$R$^{17}$, —CN, —NH$_2$, —NHR$^{17}$, or —N(R$^{17}$)$_2$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —OR$^{17}$, —CO$_2$R$^{17}$, —CN, —CF$_3$, —CON(R$^{17}$)$_2$ or $$\underset{R^{15}}{\overset{O}{\|}}$$

Q is a single bond, —(CR$^{10}$R$^{10}$)$_{\overline{p}}$ or O;

Q is a single bond, —(CR$^{10}$R$^{10}$)$_{\overline{p}}$, O, $$\underset{O'}{\overset{O}{\|}}, \quad \underset{\underset{R^{17}}{N'}}{\overset{O}{\|}};$$

p is 1 to 5;

A is —(CR$^{10}$R$^{10}$)$_q$—;

q is 2 to 5, provided that p+q is not greater than 6; and the pharmaceutically acceptable salts thereof.

8. A method according to claims 1, 2 or 3 wherein the Angiotensin (AII) Antagonist is selected from a compound of the formula:

wherein:

R is —CO$_2$H, —NHSO$_2$CF$_3$ or

X is straight or branched alkyl of 3 to 5 carbon atoms;

$R^6$ is selected from the following moieties:

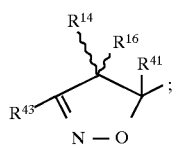
(D)

$R^{41}$ is H, straight chain lower alkyl of 1 to 4 carbon atoms, $-CF_3$, $-CN$,

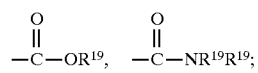

phenyl, substituted phenyl (substitution selection from mono-lower alkyl of 1 to 3 carbon atoms, $-CF_3$, nitro, O-alkyl of 1 to 3 carbon atoms), pyridine, thiophene or furan;

$R^{43}$ is $-CO_2R^{19}$,

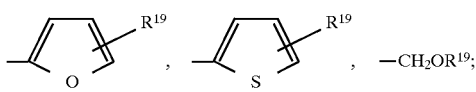

phenyl, substituted phenyl (substitution selection from mono-lower alkyl of 1 to 3 carbon atoms, $-CF_3$, nitro, O-alkyl of 1 to 3 carbon atoms), pyridine, CN, alkyl($C_1-C_6$) straight or branched,

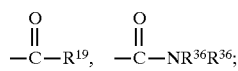

$R^{36}$ is H, straight chain or branched lower alkyl of 1 to 4 carbon atoms;

$R^{14}$ and $R^{16}$ are hydrogen, straight or branched chain lower alkyl of 1 to 4 carbon atoms, $-CO_2R^{19}$, $-CN$, phenyl, substituted phenyl (substitution selected from mono-lower alkyl of 1 to 3 carbon atoms, $-CF_3$, nitro, O-alkyl of 1 to 3 carbon atoms), pyridine, thiophene or furan,

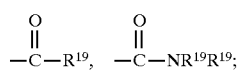

$R^{19}$ is straight or branched chain lower alkyl of 1 to 4 carbon atoms; and the pharmaceutically acceptable salts thereof.

9. A method according to claims 1, 2 or 3 wherein the Angiotensin (AII) Antagonist is selected from a compound of the formula:

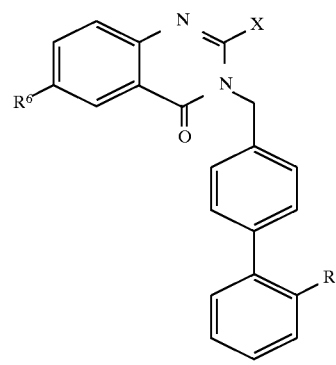

wherein:

R is $-CO_2H$, $-NHSO_2CF_3$ or

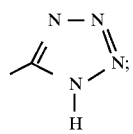

X is straight or branched alkyl of 3 to 5 carbon atoms;

$R^6$ is selected from the following moieties:

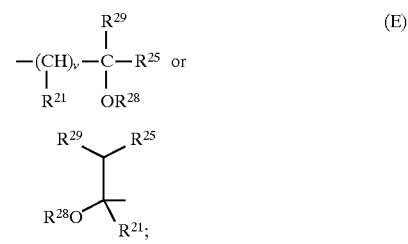
(E)

$R^{21}$, $R^{29}$ and $R^{25}$ can be the same or different;

$R^{21}$ is H, straight or branched alkyl of 1 to 4 carbon atoms, phenyl, substituted phenyl (substitution selected from mono-lower alkyl of 1 to 4 carbon atoms, $-CF_3$, nitro, $NH_2$, O-alkyl of 1 to 4 carbon atoms, F, Cl, Br), pyridine, thiophene or furan;

$R^{29}$ is H, straight chain lower alkyl of 1 to 4 carbon atoms, phenyl, substituted phenyl (substitution selected from mono-lower alkyl of 1 to 4 carbon atoms, $-CF_3$, nitro, $NH_2$, O-alkyl of 1 to 4 carbon atoms, F, Cl, Br), pyridine, thiophene or furan;

$R^{28}$ is phenyl, substituted phenyl (substitution selected from mono-lower alkyl of 1 to 4 carbon atoms, $-CF_3$, F, Cl, Br, nitro, O-alkyl of 1 to 4 carbon atoms); $R^{25}$ is straight chain lower alkyl of 1 to 4 carbon atoms, phenyl, substituted phenyl (substitution selected from mono-lower alkyl of 1 to 4 carbon atoms, $-CF_3$, nitro, O-alkyl of 1 to 4 carbon atoms, F, Cl, Br), pyridine, thiophene or furan;

v is 0 to 3; and the pharmaceutically acceptable salts thereof.

10. A method according to claims 1, 2 or 3 wherein the Angiotensin (AII) Antagonist is selected from a compound of the formula:

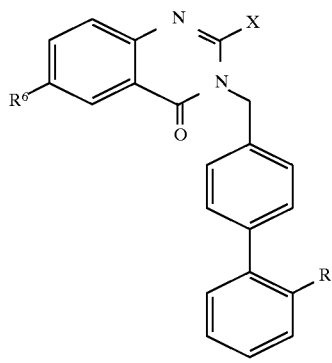

wherein:

R is —CO₂H, —NHSO₂CF₃ or

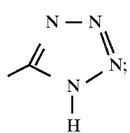

X is straight or branched alkyl of 3 to 5 carbon atoms;
R⁶ is selected from the following moieties:

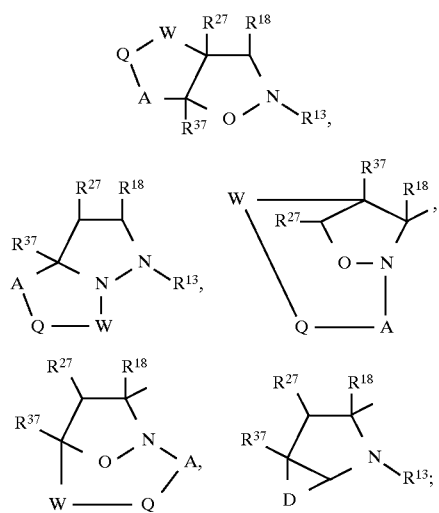

A is —(CH₂)ᵤ;
u is 1, 2, 3 or 4;
W is —CH₂— or

or A and W are each

and are connected by a —(CH₂)ᵣ— bridge, wherein r is 1, 2 or 3;

Q is —O—, —CH₂— or

D is —(CH₂)ᶠ;

f is 3 or 4;

R¹⁸ is H, lower alkyl of 1 to 4 carbon atoms (optionally substituted with OR³⁵, —CO₂R³⁵, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridine, thiophene, furan, —CHO, —CO₂R³⁵, —CN,

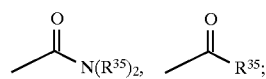

R²⁷ is H, straight chain lower alkyl of 1 to 4 carbon atoms (optionally substituted with OR³⁵, —CO₂R³⁵, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridine, thiophene or furan, —CO₂R³⁵, —CHO, —CO₂R³⁵, —CN, or

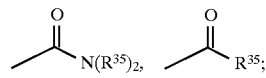

R³⁷ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene or furan, —O—R³⁵, —N(R³⁵)₂, —CO₂R³⁵, —CH₂OR³⁵, —CN, —CHO

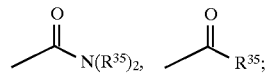

R³⁵ is independently H, lower alkyl of 1 to 4 carbon atoms;

R¹³ is H, straight chain lower alkyl of 1 to 4 carbon atoms, cycloalkyl of 5 or 6 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene or furan, benzyl, substituted benzyl (substitution selected from mono-lower alkyl of 1 to 3 carbon atoms, trifluoromethyl, nitro, O-alkyl of 1 to 3 carbon atoms, F, Cl, or Br), —CO₂R³⁵, —SO₂R³⁰

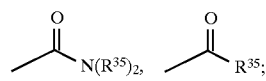

R²⁷ is H, straight or branched chain lower alkyl of 1 to 4 carbon atoms;

$R^{34}$ is H, —$CO_2R^{35}$, —$SO_2R^{30}$,

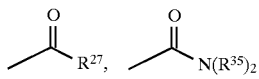

$R^{30}$ is straight or branched chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br); and the pharmaceutically acceptable salts thereof.

11. A method according to claims 1, 2 or 3 wherein the Angiotensin (AII) Antagonist is selected from a compound of the formula:

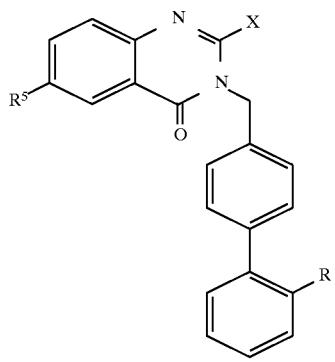

wherein:

R is —$CO_2H$, —$NHSO_2CF_3$ or

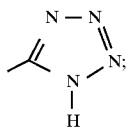

X is straight or branched alkyl of 3 to 5 carbon atoms;
$R^6$ is selected from the following moieties:

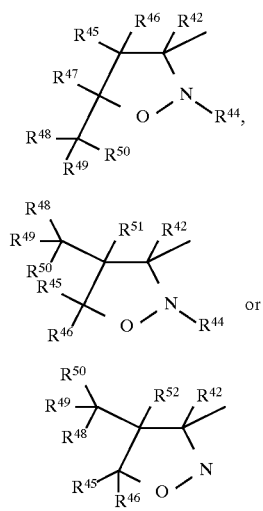

$R^{42}$ is H, straight chain lower alkyl of 1 to 4 carbon atoms, —$CF_3$, —CN,

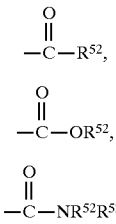

phenyl, substituted phenyl (substitution selection from mono-lower alkyl of 1 to 3 carbon atoms, —$CF_3$, nitro, O-alkyl of 1 to 3 carbon atoms), pyridine, thiophene or furan;

$R^{44}$ is straight or branched chain lower alkyl of 1 to 4 carbon atoms, cycloalkyl (rings of 3 to 8 carbon atoms), phenyl, substituted phenyl (substitution selected from mono-lower alkyl of 1 to 3 carbon atoms, —$CF_3$, nitro, O-alkyl of 1 to 3 carbon atoms), pyridine, thiophene, furan, benzyl, substituted benzyl (substitution selected from mono-lower alkyl of 1 to 3 carbon atoms, —$CF_3$, nitro, O-alkyl of 1 to 3 carbon atoms);

$R^{45}$ is H, straight or branched chain lower alkyl of 1 to 4 carbon atoms, phenyl, substituted phenyl (substitution selected from mono-lower alkyl of 1 to 3 carbon atoms, —$CF_3$, nitro, O-alkyl of 1 to 3 carbon atoms), pyridine, thiophene, furan, —CHO, —$CO_2R^{53}$, —$OR^{53}$ or

$R^{46}$ is H, straight or branched chain lower alkyl of 1 to 4 carbon atoms, phenyl, substituted phenyl (substitution selected from mono-lower alkyl of 1 to 3 carbon atoms, —$CF_3$, nitro, O-alkyl of 1 to 3 carbon atoms), pyridine, thiophene, furan, —CHO, —$OR^{53}$, —$CO_2R^{53}$ or

$R^{52}$ is hydrogen, straight chain or branched lower alkyl of 1 to 4 carbon atoms;

$R^{47}$ is H, straight or branched chain lower alkyl of 1 to 4 carbon atoms, phenyl, substituted phenyl (substitution selected from mono-lower alkyl of 1 to 3 carbon atoms, —$CF_3$, nitro, O-alkyl of 1 to 3 carbon atoms), pyridine, thiophene or furan;

$R^{48}$ is H, straight or branched chain lower alkyl of 1 to 4 carbon atoms, —$CF_3$, phenyl, substituted phenyl (substitution selected from mono-lower alkyl of 1 to 3 carbon atoms, —$CF_3$, nitro, O-alkyl of 1 to 3 carbon atoms), pyridine, thiophene, furan, benzyl, substituted benzyl(substitution selected from mono-lower alkyl of 1 to 3 carbon atoms, —$CF_3$, nitro, O-alkyl of 1 to 3 carbon atoms), —$OR^{52}$, O-phenyl, O-substituted phenyl(substitution selected from mono-lower alkyl of 1 to 3 carbon atoms, —$CF_3$, nitro, O-alkyl of 1 to 3 carbon atoms), O-pyridine, O-thiophene, O-furan, —$NH_2$, —$NHR^{53}$, —$NR^{53}R^{53}$, —$CO_2R^{53}$, or —$CONR^{52}R^{52}$;

$R^{49}$ is H, straight or branched chain lower alkyl of 1 to 4 carbon atoms, —$CF_3$, phenyl, substituted phenyl (substitution selected from mono-lower alkyl of 1 to 3 carbon atoms, —$CF_3$, nitro, O-alkyl of 1 to 3 carbon atoms), pyridine, thiophene, furan, benzyl, substituted benzyl(substitution selected from mono-lower alkyl of 1 to 3 carbon atoms, —CF$_3$, nitro, O-alkyl of 1 to 3 carbon atoms), —OR$^{52}$, O-phenyl, O-substituted phenyl(substitution selected from mono lower alkyl of 1 to 3 carbon atoms, —CF$_3$, nitro, O-alkyl of 1 to 3 carbon atoms), O-pyridine, O-thiophene, O-furan, —NH$_2$, —NHR$^{53}$, —NR$^{53}$R$^{53}$, —CO$_2$R$^{53}$, or —CONR$^{52}$R$^{52}$;

R$^{50}$ is H, straight or branched chain lower alkyl of 1 to 4 carbon atoms, —CF$_3$, phenyl, substituted phenyl (substitution selected from mono-lower alkyl of 1 to 3 carbon atoms, —CF$_3$, nitro, O-alkyl of 1 to 3 carbon atoms), pyridine, thiophene, furan, benzyl, substituted benzyl(substitution selected from mono-lower alkyl of 1 to 3 carbon atoms, —CF$_3$, nitro, O-alkyl of 1 to 3 carbon atoms), —OR$^{52}$, O-phenyl, O-substituted phenyl(substitution selected from mono-lower alkyl of 1 to 3 carbon atoms, —CF$_3$, nitro, O-alkyl of 1 to 3 carbon atoms), O-pyridine, O-thiophene, O-furan, —NH$_2$, —NHR$^{53}$, —NR$^{53}$R$^{53}$, —CO$_2$R$^{53}$, or —CONR$^{52}$R$^{52}$;

R$^{53}$ is straight or branched chain lower alkyl of 1 to 4 carbon atoms;

R$^{51}$ is —CHO, —OR$^{53}$, —CO$_2$R$^{53}$ or

and the pharmaceutically acceptable salts thereof.

12. A method according to claims 1, 2 or 3 wherein the Angiotensin (AII) Antagonist is selected from a compound of the formula:

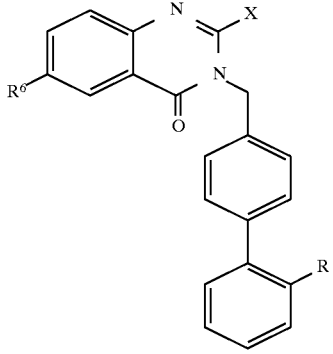

wherein:

R is —CO$_2$H, —NHSO$_2$CF$_3$ or

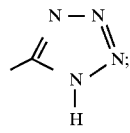

X is straight or branched alkyl of 3 to 5 carbon atoms;

R$^6$ is selected from the following moieties:

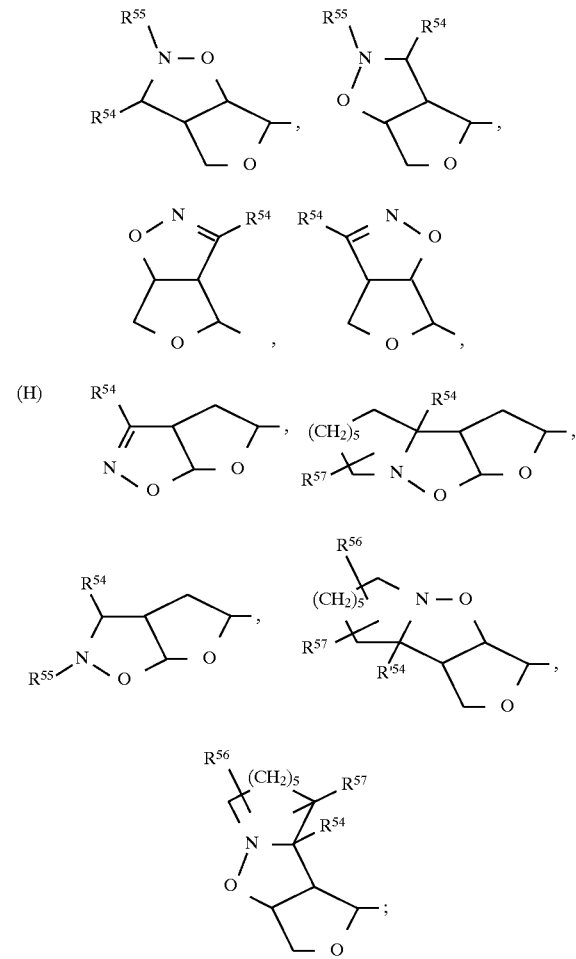

s is 1 or 2;

R$^{54}$ is straight chain lower alkyl of 1 to 4 carbon atoms (optionally substituted with —OR$^{56}$, —CO$_2$R$^{56}$, CN, phenyl, substituted phenyl (substitution selected from mono-lower alkyl of 1 to 3 carbon atoms, trifluoromethyl, nitro, O-alkyl of 1 to 3 carbon atoms, trifluoromethyl, nitro, O-alkyl of 1 to 3 carbon atoms, F, Cl, Br)), phenyl, substituted phenyl (substitution selected from mono-lower alkyl of 1 to 3 carbon atoms, trifluoromethyl, nitro, O-alkyl of 1 to 3 carbon atoms, F, Cl, Br), —CN, —CO$_2$R$^{56}$, —CHO, —CON(R$^{56}$)$_2$, Br, thiophene (optionally substituted with straight chain lower alkyl of 1 to 4 carbon atoms), furan (optionally substituted with straight chain lower alkyl of 1 to 4 carbon atoms);

R$^{55}$ is H, straight chain lower alkyl of 1 to 4 carbon atoms (optionally substituted with —OR$^{56}$, —CO$_2$R$^{56}$, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), benzyl, substituted benzyl (substitution selected from mono-lower alkyl of 1 to 3 carbon atoms, trifluoromethyl, nitro, O-alkyl of 1 to 3 carbon atoms, F, Cl, Br), —CO$_2$R$^{56}$, —SO$_2$R$^{58}$,

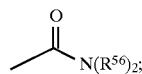

R$^{56}$ is independently H, or straight chain lower alkyl of 1 to 4 carbon atoms;

R$^{57}$ is H, straight chain lower alkyl of 1 to 4 carbon atoms;

R$^5$ is phenyl, substituted phenyl (substitution selected from mono-lower alkyl of 1 to 3 carbon atoms, trifluoromethyl, nitro, O-alkyl of 1 to 3 carbon atoms, trifluoromethyl, nitro, O-alkyl of 1 to 3 carbon atoms, F, Cl, Br)), benzyl, substituted benzyl (substitution selected from mono-lower alkyl of 1 to 3 carbon atoms, trifluoromethyl, nitro, O-alkyl of 1 to 3 carbon atoms, F, Cl,Br); and the pharmaceutically acceptable salts thereof.

13. A method according to claims 1, 2 or 3 wherein the Angiotensin (AII) Antagonist is selected from a compound of the formula:

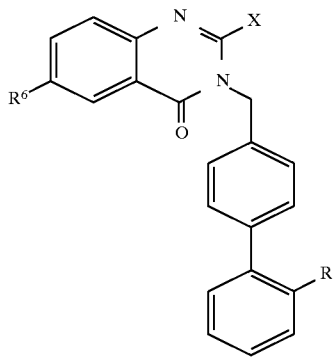

wherein:

R is —CO$_2$H, —NHSO$_2$CF$_3$ or

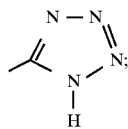

X is straight or branched alkyl of 3 to 5 carbon atoms;

R$^6$ is selected from the following moieties:

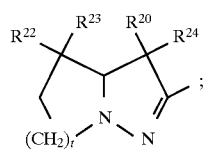

R$^{20}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R$^{24}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R$^{22}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R$^{23}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

t is 1 or 2; and the pharmaceutically acceptable salts thereof.

14. A method according to claims 1, 2 or 3 wherein the Angiotensin (AII) Antagonist is selected from a compound of the formula:

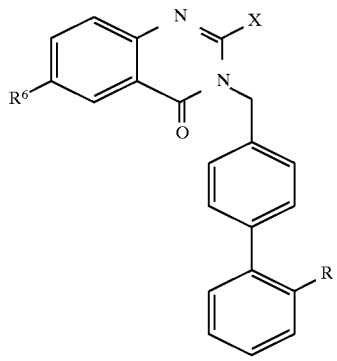

wherein:

R is —CO$_2$H, —NHSO$_2$CF$_3$ or

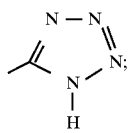

X is straight or branched alkyl of 3 to 5 carbon atoms;

R$^6$ is selected from the following moieties:

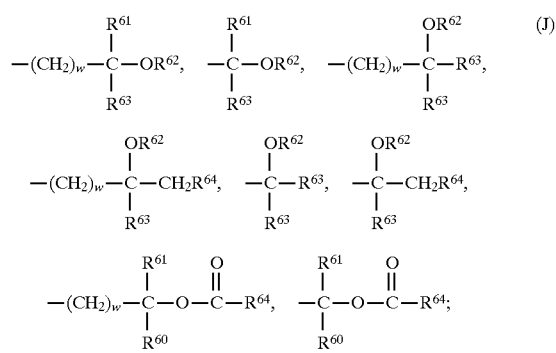

where R$^{60}$ is H, straight chain lower alkyl of 1 to 4 carbon atoms, phenyl, substituted phenyl(substitution selected from mono-lower alkyl of 1 to 3 carbon atoms, —CF$_3$, nitro, O-alkyl of 1 to 3 carbon atoms, OR, —NH$_2$), pyridine, thiophene, or furan;

R$^{61}$ is H, straight chain lower alkyl of 1 to 4 carbon atoms, phenyl, substituted phenyl (substitution selected from mono-lower alkyl of 1 to 3 carbon atoms, —CF$_3$, nitro, O-alkyl of 1 to 3 carbon atoms, OR, —NH$_2$), pyridine, thiophene, or furan; provided, however, that R$^{60}$ and R$^{61}$ cannot be H;

R$^{62}$ is H, straight chain or branched lower alkyl of 1 to 4 carbon atoms;

R$^{63}$ is straight chain lower alkyl of 1 to 4 carbon atoms, phenyl, substituted phenyl (substitution selected from mono-lower alkyl of 1 to 3 carbon atoms, —CF$_3$, nitro, O-alkyl of 1 to 3 carbon atoms, OR, —NH$_2$), pyridine, thiophene, or furan;

R$^{64}$ is straight or branched lower alkyl of 1 to 4 carbon atoms;

w is 1 to 3; and the pharmaceutically acceptable salts thereof.

15. A method according to claims 1, 2 or 3 wherein the Angiotensin (AII) Antagonist is selected from a compound of the formula:

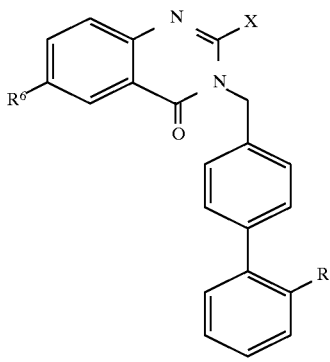

wherein:

R is —CO$_2$H, —NHSO$_2$CF$_3$ or

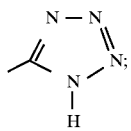

X is straight or branched alkyl of 3 to 5 carbon atoms;
R$^6$ is selected from the following moieties:

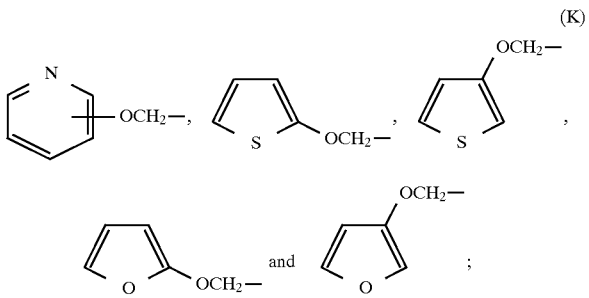

and the pharmaceutically acceptable salts thereof.

16. A method according to claims 1, 2 or 3 wherein the Angiotensin (AII) Antagonist is selected from a compound of the formula:

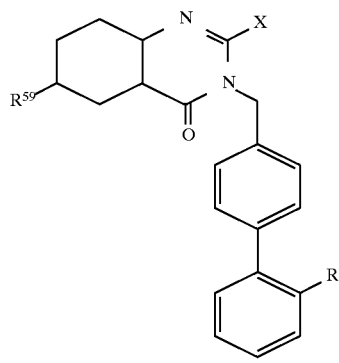

wherein:

R is —CO$_2$H, —NHSO$_2$CF$_3$ or

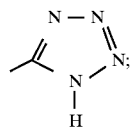

X is straight or branched alkyl of 3 to 5 carbon atoms;
R$^{59}$ is selected from the following moieties:

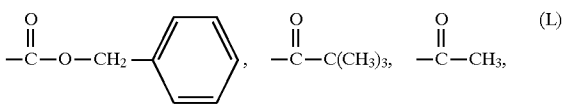

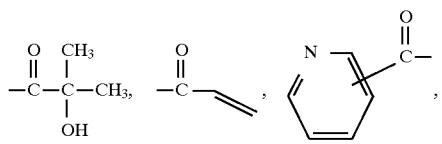

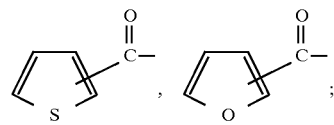

and the pharmaceutically acceptable salts thereof.

17. A method according to claim 5 wherein the compound is (3aα,6aα)-3-[2-butyl-3,4-dihydro-4-oxo-3-[[2'-(1H-tetrazol-5-yl)[1,1'-biphenyl]-4-yl]-methyl]-6-quinazolinyl]-2,3,3a,6a-tetrahydro-3,5-di-methylpyrrolo[3,4-c]pyrazole-4,6-(1H,5H)-dione.

18. A method according to claim 6 wherein the compound is 2-butyl-6-[hydroxy(tetrahydro-2-thienyl)methyl]-3-[[2'-(1H-tetrazol-5-yl)[1,1'-biphenyl]-4-yl]methyl]-4(3H)-quinazolinone S,S-dioxide isomer 1.

19. A method according to claim 6 wherein the compound is 2-butyl-6-[hydroxy(tetrahydro-2-thienyl)methyl]-3-[[2'-(1H-tetrazol-5-yl)[1,1'-biphenyl]-4-yl]methyl]-4(3H)-quinazolinone S,S-dioxide isomer 2.

20. A method according to claim 6 wherein the compound is 2-butyl-6-[1-hydroxy-1-(1-methyl-2-oxo-3-pyrrolidinyl) ethyl]-3-[[2'-(1H-tetrazol-5-yl)[1,1'-biphenyl]-4-yl]methyl]-4(3H)-quinazolinone isomer 1.

21. A method according to claim 7 wherein the compound is trans-(±)-2-[2-butyl-3,4-dihydro-4-oxo-3-[[2'-(1H-tetrazol-5-yl)[1,1'-biphenyl]-4-yl]-methyl]-6-quinazolinyl] hexahydropyrrolo[1,2-b]isoxazole-2-carboxylic acid methyl ester monohydro.

22. A method according to claim 7 wherein the compound is cis-(±)-2-butyl-6-(hexahydro-2-methylpyrrolo[1,2-b]isoxazol-2-yl)-3-[[2'-(1H-tetrazol-5-yl)[1,1-biphenyl]-4-yl]methyl]-4(3H)-quinazolinone sodium salt.

23. A method according to claim 8 wherein the compound is 2-butyl-6-[4,5-dihydro-3-(4-methylphenyl)-5-isoxazolyl]- 3-[[2'-(1H-tetrazol-5-yl)[1,1'-biphenyl]-4-yl]methyl]-4(3H)-quinazolinone.

24. A method according to claim 8 wherein the compound is 5-[2-butyl-3,4-dihydro-4-oxo-3-[[2'-(1H-tetrazol-5-yl)[1,1'-biphenyl]-4-yl]methyl]-6-quinazolinyl]-4,5-dihydro-5-methyl-3-isoxazolecarboxylic acid ethyl ester.

25. A method according to claim 9 wherein the compound is 2-butyl-6-(phenoxymethyl)-3-[[2'-(1H-tetrazol-5-yl)[1,1'-biphenyl]-4-yl]-methyl]-4(3H)-quinazolinone.

26. A method according to claim 11 wherein the compound is (3S-trans)-2-butyl-6-[5-(hydroxymethyl)-2-methyl-3-isoxazolidinyl]-3-[[2'-(1H-tetrazol-5-yl)[1,1'-biphenyl]-4-yl]methyl]-4(3H)-quinazolinone.

27. A method according to claim 11 wherein the compound is (3R-cis)-2-butyl-6-[5-(hydroxymethyl)-2-methyl-3-isoxazolidinyl]-3-[[2'-(1H-tetrazol-5-yl)-[1,1'-biphenyl]-4-yl]methyl]-4(3H)-quinazolinone.

28. A method according to claim 12 wherein the compound is [2S-(2α,3aα,3bβ,8aα)]-2-butyl-6-(6,6-dimethyloctahydrofuro[3,2-d]pyrrolo-[1,2-d]isoxazol-2-yl)-3-[[2'-(1H-tetrazol-5-yl)[1,1'-biphenyl]-4-yl]methyl]-4(3H)-quinazolinone.

29. A method according to claim 13 wherein the compound is 2-butyl-6-(3,3a,4,5,6,7-hexahydropyrazolo[1,5-a]pyridin-2-yl)-3-[[2'-(1H-tetrazol-5-yl)[1,1'-biphenyl]-4-yl]methyl]-4(3H)-quinazolinone.

30. A method according to claim 15 wherein the compound is 2-butyl-6-[(2-pyridinyloxy)methyl]-3-[[2'-(1H-tetrazol-5-yl)[1,1'-biphenyl]-4-yl]methyl]-4(3H)-quinazolinone hydrochloride.

31. A method according to claim 16 wherein the compound is 2-butyl-3,5,7,8-tetrahydro-3-[[2'-(1H-tetrazol-5-yl)[1,1,'-biphenyl]-4-yl]methyl]-pyrido[4,3-d]pyrimidin-6(4H)-carboxylic acid phenylmethyl ester.

32. A method according to claim 16 wherein the compound is 2-butyl-5,6,7,8-tetrahydro-6-(2-hydroxy-2-methyl-1-oxopropyl)-3-[[2'-(1H-tetrazol-5-yl)[1,1'-biphenyl]-4-yl]methyl]-4(3H)-quinazolinone.

33. A method according to claim 4 wherein the compound is 2-n-butyl-4-chloro-5-hydroxymethyl-1-[(2'-(1H-tetrazol-5-yl)biphenyl-4-yl)methyl]imidazole.

34. A method according to claim 4 wherein the compound is ((S)-)-[[4-(dimethylamino)-3-methylphenyl]methyl-5-[diphenylacetyl)-4,5,6,7-tetrahydro-1H-imidazo[4,5-c]pyridine-6-carboxylic acid.

35. A method according to claim 1 wherein the compound is 5-methyl-7-propyl-8-[(2'-(1H-tetrazol-5-yl)biphenyl-4-yl)methyl]-1,2,4-triazolo[1,5-c]pyrimidin-2(3H)-one.

36. A method according to claim 2 wherein the compound is 5-methyl-7-propyl-8-[(2'-(1H-tetrazol-5-yl)biphenyl-4-yl)methyl]-1,2,4-triazolo[1,5-c]pyrimidin-2(3H)-one.

37. A method according to claim 4 wherein the compound is 2-ethyl-5,7-dimethyl-3-[[2'-(1H-tetrazol-5-yl)[1,1'-biphenyl]-4-yl]methyl]-3H-imidazo-[4,5-b]pyridine.

\* \* \* \* \*